United States Patent

Sakane et al.

Patent Number: 5,302,712
Date of Patent: Apr. 12, 1994

[54] INTERMEDIATES FOR CEPHEM COMPOUNDS

[75] Inventors: Kazuo Sakane; Kohji Kawabata, both of Kawanishi; Yoshiko Inamoto, Toyonaka, all of Japan

[73] Assignee: Fujisawa Pharmaceutical Co., Ltd., Osaka, Japan

[21] Appl. No.: 21,470

[22] Filed: Feb. 23, 1993

Related U.S. Application Data

[62] Division of Ser. No. 604,632, Oct. 26, 1990, Pat. No. 5,215,982.

[30] Foreign Application Priority Data

Nov. 10, 1989 [GB] United Kingdom ............... 8925404
Jan. 25, 1990 [GB] United Kingdom ............... 9001778
Jul. 30, 1990 [GB] United Kingdom ............... 9016688

[51] Int. Cl.$^5$ .................................. C07D 501/18
[52] U.S. Cl. ............................ 540/222; 514/202
[58] Field of Search ............... 540/222, 221; 514/202

[56] References Cited

U.S. PATENT DOCUMENTS

4,962,100 10/1990 Miyake et al. ............... 540/222
5,215,982 6/1993 Sakane et al. ............... 540/222
5,219,848 6/1993 Denneguin et al. ............ 540/222

Primary Examiner—Nicholas S. Rizzo
Attorney, Agent, or Firm—Oblon, Spivak, McClelland, Maier & Neustadt

[57] ABSTRACT

The invention relates to compounds, useful as intermediates in the preparation of products of antimicrobial activity, of the formula:

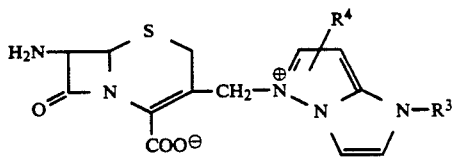

wherein
$R^3$ is hydrogen, lower alkyl, hydroxy(lower)alkyl, protected hydroxy(lower)alkyl, amino(lower)alkyl, protected amino (lower) alkyl, carbamoyl)-lower)alkyl, N,N-di(lower) alkylcarbamoyl(lower)alkyl or an amino protective group, and
$R^4$ is hydrogen, lower alkyl, carboxy, protected carboxy, amino, protected amino or carbamoyl, or a salt thereof.

1 Claim, No Drawings

INTERMEDIATES FOR CEPHEM COMPOUNDS

This is a division of U.S. patent application Ser. No. 07/604,632, filed on Oct. 26, 1990, now 5,215,982.

The present invention relates to new cephem compounds and pharmaceutically acceptable salts thereof.

More particularly, it relates to new cephem compounds and pharmaceutically acceptable salts thereof, which have antimicrobial activities, to processes for preparation thereof, to pharmaceutical composition comprising the same, and to a method for treating infectious diseases in human being and animals.

Accordingly, one object of the present invention is to provide the cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula (I):

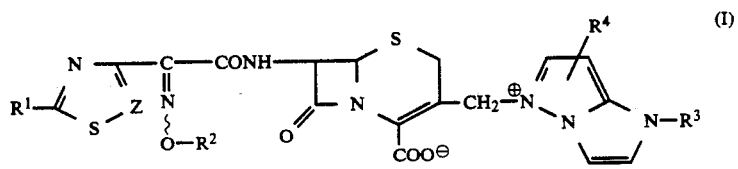

wherein
- $R^1$ is amino or a protected amino group,
- $R^2$ is hydrogen or an organic group,
- $R^3$ is hydrogen, lower alkyl, hydroxy(lower)alkyl, protected hydroxy(lower)alkyl, amino(lower)alkyl, protected amino(lower)alkyl, carbamoyl(lower)alkyl, N,N-di(lower)alkylcarbamoyl(lower)alkyl or an imino protective group,
- $R^4$ is hydrogen, lower alkyl, carboxy, protected carboxy, amino, protected amino or carbamoyl, and
- Z is N or CH.

The cephem compound (I) of the present invention can be prepared by processes as illustrated in the following.

Process 1

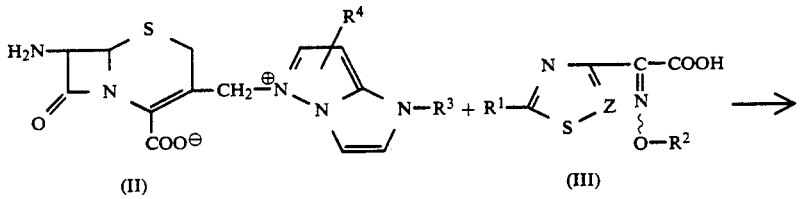

(II)
or its reactive derivative
at the amino group
or a salt thereof (III)
or its reactive derivative
at the carboxy group
or a salt thereof

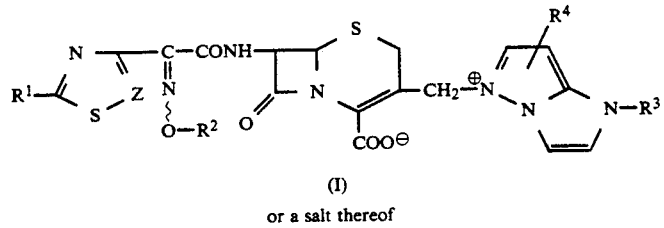

(I)
or a salt thereof

Process 2

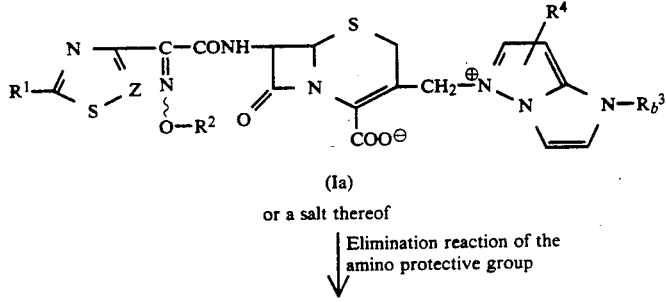

(Ia)
or a salt thereof

↓ Elimination reaction of the amino protective group

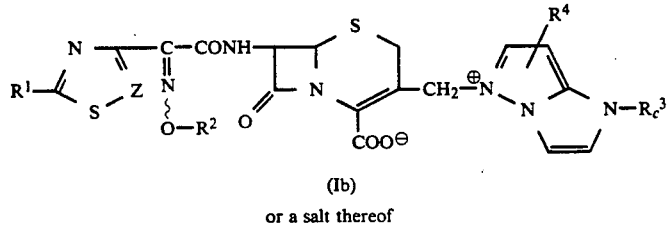
(Ib)
or a salt thereof
Process 3
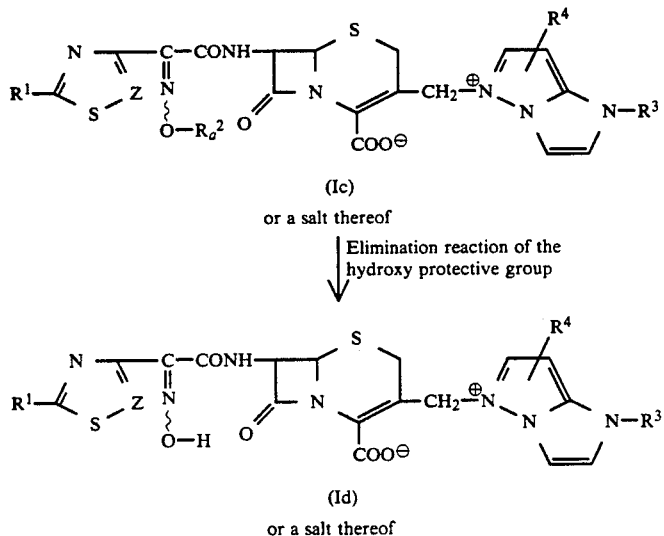
wherein
R¹, R², R³, R⁴ and Z are each as defined above,
$R_b^3$ is protected amino(lower)alkyl,
$R_c^3$ is amino(lower)alkyl and
$R_a^2$ is hydroxy protective group.
The starting compound (II) is novel and can be prepared by processes as illustrated in the following.
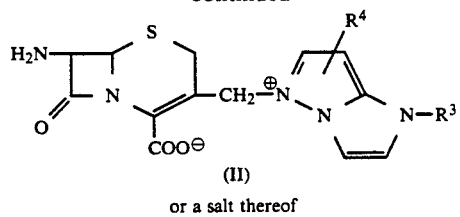
(II)
or a salt thereof
Process B
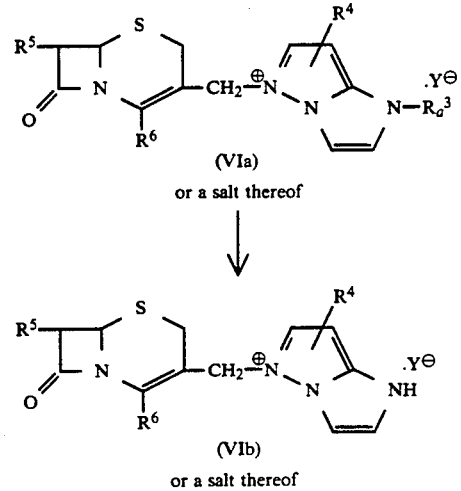
Process C
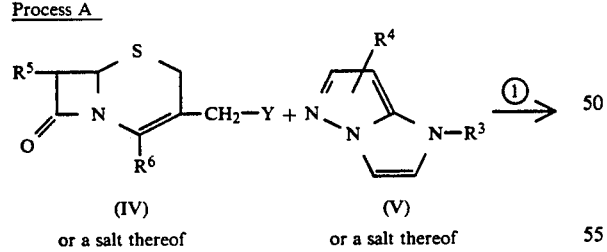

-continued

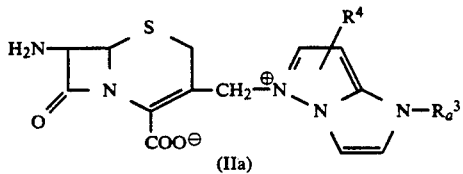

(IIa)

or a salt thereof

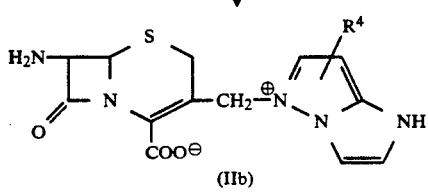

(IIb)

or a salt thereof wherein
R³ and R⁴ are each as defined above,
R⁵ is a protected amino group,
R⁶ is a protected carboxy group,
Y is an acid residue, and
$R_a^3$ is an imino protective group.

Further, the compound (V) or a salt thereof can be prepared by the methods disclosed in the Preparations 1-4, 11-22, 31-52 and 58 described later or similar manners thereto.

Regarding the compounds (I), (Ia)-(Id) and (III), it is to be understood that said compounds include syn isomer, anti isomer and a mixture thereof. For example, with regard to the object compound (I), syn isomer means one geometrical isomer having the partial structure represented by the following formula:

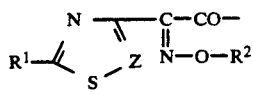

(wherein R¹, R² and Z are each as defined above) and anti isomer means the other geometrical isomer having the partial structure represented by the following formula:

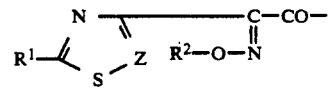

(wherein R¹, R² and Z are each as defined above).

Regarding the other compounds, as mentioned above, the syn isomer and the anti isomer can also be referred to the same geometrical isomers as illustrated for the compound (I).

Further, it is to be noted that the compound (I) can also exist in the tautomeric form, and such tautomeric equilibrium can be represented by the following schems.

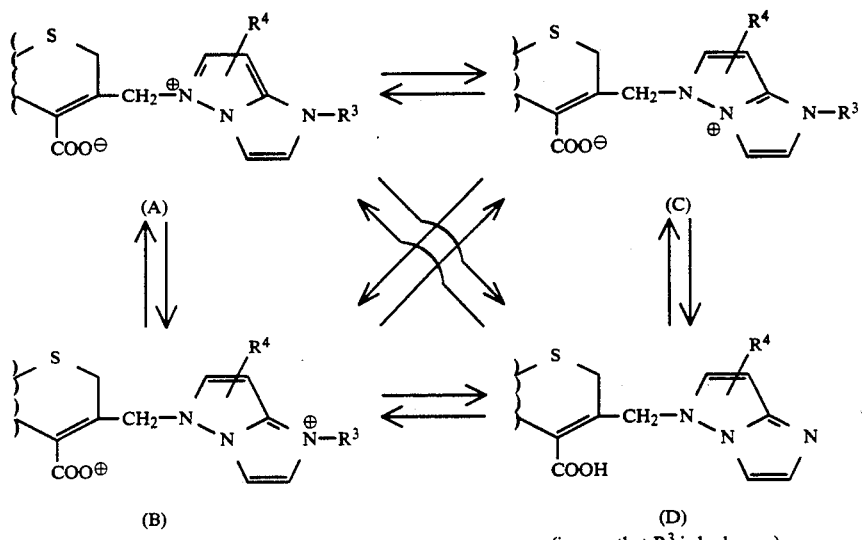

(in case that R³ is hydrogen)

All of the above tautomeric isomers are included within the scope of the present invention, and in the present specification and claim, however, the object compound (I) is represented for the convenient sake by the formula (A).

Suitable pharmaceutically acceptable salts of the object compound (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean a group having 1 to 6 carbon atom(s) preferably 1 to 4 carbon atom[s], unless otherwise provided.

Suitable "protected amino" and "protected amino moiety" in the term "protected amino(lower)alkyl" may include an acylamino or an amino group substituted by a conventional protective group such as ar(lower)alkyl which may have suitable substituent(s) (e.g. benzyl, trityl, etc.) or the like.

Suitable "acyl moiety" in the term "acylamino" may include carbamoyl, substituted carbamoyl, aliphatic acyl group and acyl group containing an aromatic or heterocyclic ring. And, suitable examples of the said acyl may be N,N-di(lower)alkylcarbamoyl, lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.); lower alkanesulfonyl (e.g. mesyl, ethanesulfonyl, propane-sulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc), and the like. The acyl moiety as stated above may have suitable substituent(s) such as halogen (e.g. chlorine, bromine, iodine or fluorine) or the like.

Suitable "organic group" may include lower alkyl, mono[or di or tri)halo(lower)alkyl (e.g. chloromethyl, dichloromethyl, trichloromethyl, bromomethyl, chloroethyl, dichloroethyl, trichloroethyl, fluoroethyl, trifluoroethyl, etc.), lower alkenyl (e.g., vinyl, 1-propenyl, allyl, 1-methylallyl, 1 or 2 or 3 butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), aryl (e.g., phenyl, naphthyl, etc.), ar(lower)alkyl such as phenyl(lower)alkyl (e.g., benzyl, phenethyl, phenylpropyl, etc.), carboxy(lower)alkyl, protected carboxy(lower)alkyl, hydroxy(lower)alkyl, protected hydroxy(lower)alkyl, hydroxy protective group, and the like.

Suitable "protected carboxy" and "protected carboxy moiety" in the term "protected carboxy(lower)alkyl" may include esterified carboxy and the like. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.); lower alkenyl ester (e.g., vinyl ester, allyl ester, etc.); lower alkynyl ester (e.g. ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.); mono(or di or tri)-halo(lower)alkyl ester (e.g. 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoylcxymethyl ester, 2-acetoxyethyl ester, 2-propionyloxyethyl ester, etc.); lower alkanesulfonyl(lower)alkyl ester (e.g., mesylmethyl ester, 2-mesylethyl ester etc.); ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g. phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Suitable "lower alkyl" and "lower alkyl moiety" in the terms "carboxy(lower)alkyl", "protected carboxy(lower)alkyl", "hydroxy(lower)alkyl", "protected hydroxy(lower)alkyl", "amino(lower)alkyl", "protected amino(lower)alkyl", "carbamoyl(lower)alkyl", "N,N-di(lower)alkylcarbamoyl(lower)alkyl" and "N,N-di(lower)alkylcarbamoyl" may include straight or branched one such as methyl, ethyl, propyl, isopropyl, butyl, isobutyl, tert-butyl, pentyl, hexyl or the like.

Suitable "imino protective group" may include an acyl group as exemplified above, and the like.

Suitable "hydroxy protective group" may include an acyl group as exemplified above, and the like.

Suitable "protected hydroxy moiety" in the term "protected hydroxy(lower)alkyl" may be acyloxy group or the like.

Suitable "acyl moiety" in the term "acyloxy" may include an acyl group as exemplified above, and the like.

Suitable "acid residue" may include halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.] or the like.

The processes for preparing the object compound of the present invention are explained in detail in the following.

PROCESS 1

The compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)-acetamide, mono(trimethylsilyl)acetamide [e.g. N-(trimethylsilyl)acetamide], bis(trimethylsilyl)urea or the like; a derivative formed by reaction of the compound (II) with phosphorus trichloride or phosgene, and the like.

Suitable salts of the compound (II) and its reactive derivative can be referred to the ones as exemplified for the compound (I).

Suitable reactive derivative at the carboxy group of the compound (III) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of thecompound (III) and its reactive derivative can be referred to the ones as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; thionyl chloride, oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 2

The compound (Ib) or a salt thereof can be prepared by subjecting the compound (Ia) or a salt thereof to elimination reaction of the amino protective group.

Suitable method of this elimination reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.]and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts [e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

PROCESS 3

The compound (Id) or a salt thereof can be prepared by subjecting the compound (Ic) or a salt thereof to elimination reaction of the hydroxy protective group. This reaction can be carried out in a similar manner to that of the aforementioned Process 2, and therefore the reagent to be used and the reaction conditions (e.g., solvent, reaction temperature, etc.) can be referred to those of the Process 2.

The processes for preparing the starting compounds are explained in the following.

PROCESS A - ①

The compound (VI) or a salt thereof can be prepared by reacting the compound (IV) or a salt thereof with the compound (V) or a salt thereof.

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction. The reaction temperature is not critical, and the reaction is usually carried out at ambient temperature, under warming or under heating.

PROCESS A - ②

The compound (II) or a salt thereof can be prepared by subjecting the compound (VI) or a salt thereof to elimination reaction of the amino protective group in $R^5$ and the carboxy protective group in $R^6$.

This reaction can be carried out in a similar manner to that of the aforementioned Process 2, and therefore the reagent to be used and the reaction conditions (e.g., solvent, reaction temperature, etc.) can be referred to those of the Process 2.

PROCESS B

The compound (VIb) or a salt thereof can be prepared by subjecting the compound (VIa) or a salt thereof to elimination reaction of the imino protective group. This reaction can be carried out in a similar manner to that of the aforementioned Process 2, and therefore the reagent to be used and the reaction conditions (e.g., solvent, reaction temperature, etc.) can be referred to those of the Process 2.

PROCESS C

The compound (IIb) or a salt thereof can be prepared by subjecting the compound (IIa) or a salt thereof to elimination reaction of the imino protective group. This reaction can be carried out in a similar manner to that of the aforementioned Process 2, and therefore the reagent to be used and the reaction conditions (e.g., solvent, reaction temperature, etc.) can be referred to those of the Process 2.

The object compound (I) and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on MIC (minimal inhibitory concentration) of a representative compound of the compound (I) are shown in the following.

TEST METHOD

In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

TEST COMPOUND (1)

7β-[2-(5-Amino-1,2,4-thiadiazol-3-yl)-2-methoxyiminoacetamido]-3-[5-(1H-imidazo[1,2-b]pyrazolio)]methyl-3-cephem-4-carboxylate (syn isomer)

TEST RESULT

| | MIC (μg/ml) |
| Test strain | Test Compound (1) |
| --- | --- |
| E. coli 31 | ≦0.025 |

For therapeutic administration, the object compound (I) and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc., in general, amounts between 1 mg and about 4,000 mg or even more per day may be administered to a patient. An average single dose of about 50 mg, 100 mg, 250 mg, 500 mg, 1000 mg, of the object compound (I) of the present invention may be used in treating diseases infected by pathogenic microorganisms.

The following Preparations and Examples are given for the purpose of illustrating the present invention more detail.

PREPARATION 1

A mixture of hydrazinoacetaldehyde diethyl acetal (21 g) and methoxyacrylonitrile (11.8 g) in water (150 ml) was refluxed for 2 days. After the reaction mixture was cooled, to the mixture was added a mixture of water and ethyl acetate. The separated organic layer was washed with brine and dried over magnesium sulfate. The solvent was evaporated and the residue was subjected to column chromatography on silica gel using ethyl acetate as an eluent. Fractions containing the object compound were combined and evaporated to give 1-(2,2-diethoxyethyl)-5-aminopyrazole (5.45 g).

IR (Nujol) : 3300–3400, 2970, 1620, 1550, 1500 cm$^{-1}$.

NMR (DMSO-d$_6$, δ) : 1.06 (6H, t, J=7Hz), 3.31-3.4-8 (2H, m), 3.54–3.69 (2H, m), 3.80 (2H, d, J=7Hz), 4.75 (1H, t, J=7Hz), 5.02 (2H, br s), 5.26 (1H, d, J=2Hz), 7.08 (1H, d, J=2Hz)

PREPARATION 2

To a solution of 1-(2,2-diethoxyethyl)-5-aminopyrazole (5.4 g) in ethanol (420 ml) was added aqueous 20% sulfuric acid solution (108 ml). The mixture was refluxed for 3 hours. After the reaction mixture was cooled, the mixture was adjusted to pH 8 with sodium carbonate (62 g). The insoluble material was filtered off and the filtrate was evaporated to give 1H-imidazo[1,2-b]pyrazole (2.14 g).

NMR (DMSO-d$_6$, δ) : 5.62 (1H, d, J=2Hz), 7.14 (1H, br s), 7.45 (1H, d, J=2Hz), 7.49 (1H, br s), 10.97 (1H, br s).

PREPARATION 3

A mixture of acetic anhydride (3.68 ml) and formic acid (3 ml) was stirred at room temperature for 1 hour. The solution was cooled in an ice-bath and 1H-imidazo-[1,2-b]pyrazole (2.1 g) was added thereto. The mixture was stirred at room temperature for 1 hour. The reaction mixture was evaporated and the residue was subjected to column chromatography on silica gel using a mixture of n-hexane and ethyl acetate (1:1) as an eluent. Fractions containing the object compound were combined and the solvent was evaporated to give 1-formyl-1H-imidazo[1,2-b]pyrazole (1.83 g). NMR (DMSO-d$_6$, δ) : 6.20 and 6.28 (total 1H, each d, J=2Hz), 7.65-7.72 (1H, m), 7.71 (1H, d, J=2Hz), 7.87-7.92 (1H, m), 9.02 (1H, br s)

PREPARATION 4

The following compound was obtained according to a similar manner to that of Preparation 3.

1-Formyl-6-methyl-1H-imidazo[1,2-b]pyrazole

NMR (DMSO-d$_6$, δ): 2.32 (3H, s), 6.07 (1H, s), 7.43-7.63 (1H, m), 7.63-7.80 (1H, m), 8.98 (1H, br s)

PREPARATION 5

To a solution of benzhydryl 7β-t-butoxycarbonylamino-3-chloromethyl-3-cephem-4-carboxylate (4.57 g) in N,N-dimethylformamide (5 ml) was added sodium iodide (1.33 g). After the mixture was stirred at room temperature for 30 minutes, 1-formyl-1H-imidazo[1,2-b]pyrazole (1.8 g) was added thereto. The mixture was stirred at the same condition for 20 hours. The reaction mixture was poured into a mixture of ethyl acetate (200 ml) and water (100 ml). The separated organic layer was washed with water and then brine, and dried over magnesium sulfate. The solvent was evaporated on vacuo, and the residue was pulverized with diisopropyl ether and collected by filtration to give benzhydryl 7β-t-butoxycarbonylamino-3-[1-formyl-5-(1H-imidazo[1,2-b]pyrazolio)]methyl-3-cephem-4-carboxylate iodide (4.7 g).

IR (Nujol) : 1780, 1610 cm$^{-1}$

NMR (DMSO-d$_6$, δ): 1.40 (9H, s), 3.38 (2H, br s), 5.15 (1H, d, J=5Hz), 5.28 and 5.45 (2H, ABq, J=16Hz), 5.60 (1H, dd, J=5Hz, 8Hz), 6.59 (1H, d, J=3Hz), 6.96 (1H, s), 7.00-7.60 (11H, m), 7.71 (1H, br s), 8.06 (1H, d, J=8Hz), 8.50 (1H, br s)

PREPARATION 6

The following compound was obtained according to a similar manner to that of PREPARATION 5.

Benzhydryl 7β-t-butoxycarbonylamino-3-[1-formyl-6-methyl-5-(1H-imidazo[1,2-b]pyrazolio)]methyl-3-cephem-4-carboxylate iodide IR (Nujol): 1775, 1710, 1590 cm$^{-1}$ NMR (DMSO-d$_6$) : 1.40 (9H, s), 2.28 (3H, s), 3.29–3.50 (2H, br s), 5.15 (1H, d, J=5Hz), 5.39 (2H, br s), 5.64 (1H, dd, J=5Hz, 8Hz), 6.98 (1H, s), 7.10-7.60 (11H, m), 7.61 (1H, d, J=2Hz), 7.88 (1H, d, J=3Hz), 8.10 (1H, d, J=8Hz), 8.50 (1H, br s)

PREPARATION 7

To a suspension of benzhydryl 7β-t-butoxycarbonyl-amino-3-[1-formyl-5-(1H-imidazo[1,2-b]pyrazolio)]-methyl-3-cephem-4-carboxylate iodide (4.5 g) in a mixture of anisole (5 ml) and methylene chloride (15 ml) was added dropwise trifluoroacetic acid (9 ml) under ice-cooling. The mixture was stirred at room temperature for 2 hours. The reaction mixture was poured into a mixture of diisopropyl ether (150 ml) and ethyl acetate (150 ml). The resultant powder was collected by filtration and washed with diisopropyl ether and dried over phosphorus pentoxide in vacuo to give 7β-amino-3-[1-formyl-5-(1H-imidazo[1,2-b]pyrazolio)]methyl-3-cephem-4-carboxylate bis(trifluoroacetate) (3.12 g).

IR (Nujol) : 1780, 1660, 1590 cm$^{-1}$

NMR (DMSO-d$_6$,δ) : 3.40 and 3.56 (2H, ABq, J=18Hz), 5.05-5.5 (4H, m), 6.64 (1H, d, J=3Hz), 7.78 (1H, br s), 8.07 (1H, br s), 8.27 (1H, d, J=3Hz), 8.50 (1H, br s)

PREPARATION 8

The following compound was obtained according to a similar manner to that of Preparation 7.

7β-Amino-3-[1-formyl-6-methyl-5-(1H-imidazo[1,2-b]-pyrazolio)]methyl-3-cephem-4-carboxylate bis(trifluoroacetate)

NMR (DMSO-d$_6$, δ) : 2.50 (3H, s), 3.32 and 3.48 (2H, ABq, J=1.8Hz), 5.00-5.50 (4H, m), 6.50 (1H, d, J=3Hz), 7.71 (1H, br s), 8.05 (1H, br s), 8.50 (1H, br s).

PREPARATION 9

To a suspension of 7β-amino-3-[1-formyl-5-(1H-imidazo[1,2-b]pyrazolio)]methyl-3-cephem-4-carboxylate bis(trifluoroacetate) (3.0 g) in methanol (15 ml) was added conc. hydrochloric acid (1.5 ml). The mixture was stirred at room temperature for 2 hours. The reaction mixture was added dropwise to ethyl acetate (150 ml). The resultant powder was collected by filtration and washed with diisopropyl ether and dried over phosphorus pentoxide in vacuo to give 7β-amino-3-[5-(1H-imidazo[1,2-b]-pyrazolio)]methyl-3-cephem-4-carboxylate trihydrochloride (1.77 g).

NMR (D$_2$O-NaHCO$_3$, δ) : 3.09 and 3.40 (2H, ABq, J=18Hz), 4.40-5.50 (4H, m), 6.42 (1H, d, J=3Hz), 7.45

(1H, d, J=2Hz), 7.86 (1H, d, J=2Hz), 7.99 (1H, d, J=3Hz).

PREPARATION 10

The following compound was obtained according to a similar manner to that of Preparation 9.

7β-Amino-3-[6-methyl-5-(1H-imidazo[1,2-b]pyrazolio)]-methyl-3-cephem-4-carboxylate trihydrochloride IR (Nujol) : 1780, 1700, 1600 cm$^{-1}$.

NMR (D$_2$O, δ) : 2.63 (3H, s), 3.30 and 3.57 (2H, ABq, J=18Hz), 5.07-5.67 (4H, m), 6.37 (1H, br s), 7.48 (1H, d, J=2Hz), 7.89 (1H, d, J=2Hz)

EXAMPLE 1

To a solution of 7β-amino-3-[5-(1H-imidazo[1,2-b]pyrazolio)]methyl-3-cephem-4-carboxylate trihydrochloride (0.9 g), N-trimethylsilylacetamide (2.8 g) and tetrahydrofuran (20 ml) was added 2-(5-amino-1,2,4-thiadiazol-3-yl)-2-methoxyiminoacetyl chloride hydrochloride (syn isomer) (0.59 g) under ice-cooling. The mixture was stirred at room temperature for 2 hours. The reaction mixture was poured into ethyl acetate (200 ml). The resultant precipitate was collected by filtration and washed with diisopropyl ether and dried over phosphorus pentoxide in vacuo. The powder was added to water and adjusted to pH 2.5 with 1N hydrochloric acid and the insoluble material was filtered off. The aqueous solution was subjected to column chromatography on Diaion HP-20 [Trademark : prepared by Mitsubishi Kasei Corporation] using aqueous 5% isopropyl alcohol solution as an eluent. Fractions containing the object compound were combined, evaporated in vacuo to remove isopropyl alcohol and lyophilized to give 7β-[2-(5-amino-1,2,4-thiadiazol-3-yl)-2-methoxyiminoacetamido]-3-[5-(1H-imidazo[1,2-b]pyrazolio)]-methyl-3-cephem-4-carboxylate (syn isomer) (0.13 g).

IR (Nujol) : 1760, 1670, 1600 cm$^{-1}$

NMR (D$_2$O-NaHCO$_3$, δ) : 3.77, 3.33 (2H, ABq, J=18Hz), 4.03 (3H, s), 5.13 (1H, d, J=5Hz), 5.22 (2H, br s), 5.80 (1H, d, J=5Hz), 6.32 (1H, d, J=2Hz), 7.36 (1H, br s), 7.77 (1H, br s), 7.88 (1H, d, J=2Hz).

EXAMPLE 2

A solution of 7β-amino-3-[5-(1H-imidazo[1,2-b]pyrazolio)]methyl-3-cephem-4-carboxylate trihydrochloride (0.8 g) in a mixture of water (8 ml) and tetrahydrofuran (16 ml) was adjusted to pH 7 with a saturated aqueous sodium bicarbonate solution and 1-[2-(2-aminothiazol-4-yl)-2-methoxyiminoacetyl]-1H-benzotriazol-3-oxide (1.1 g) was added thereto at room temperature. The mixture was stirred for 5 hours at 30° C. under pH 7. To the reaction mixture was added ethyl acetate (15 ml) and the separated aqueous layer was washed with ethyl acetate (15 ml×2). The aqueous solution was adjusted to pH 4 with N hydrochloric acid and washed with ethyl acetate (15 ml×3). The aqueous solution was adjusted to pH 2 with 1N hydrochloric acid, and subjected to column chromatography on Diaion HP-20 (30 ml) using 10% isopropyl alcohol as an eluent. Fractions containing the object compound were combined, concentrated to remove isopropyl alcohol and lyophilized to give 7β-[2-(2-aminothiazol-4-yl)-2-methoxyiminoacetamido]-3-[5-(1H-imidazo[1,2-b]-pyrazolio)]-methyl-3-cephem-4-carboxylate (syn isomer) (0.26 g).

IR (Nujol) : 1770, 1670, 1600 cm$^{-1}$.

NMR (D$_2$O-NaHCO$_3$, δ): 2.93 and 3.23 (2H, ABq, J=18Hz), 3.83 (3H, s), 5.02 (1H, d, J=5Hz), 5.11 (2H, br s), 5.65 (1H, d, J=5Hz), 6.21 (1H, d, J=3Hz), 6.74 (1H, s), 7.20 (1H, d, J=2Hz), 7.70 (1H, d, J=2Hz), 7.80 (1H, d, J=3Hz).

EXAMPLE 3

The following compounds were obtained according to similar manners to those of Examples 1 and 2.

(1)

7β-[2-(5-Amino-1,2,4-thiadiazol-3-yl)-2-methoxyiminoacetamido]-3-[6-methyl-5-(1H-imidazo[1,2-b]-pyrazolio)]methyl-3-cephem-4-carboxylate (syn isomer)

IR (Nujol) : 1760, 1660, 1600 cm$^{-1}$.

NMR (D$_2$O-NaHCO$_3$, δ): 2.48 (3H, s), 3.00 and 3.29 (2H, ABq, J=18Hz), 4.05 (3H, s), 5.14 (1H, d, J=5Hz), 5.21 (2H, br s), 5.82 (1H, d, J=5Hz), 6.15 (1H, br s), 7.28 (1H, d, J=2Hz), 7.75 (1H, d, J=2Hz).

(2)

7β-[2-(2-Aminothiazol-4-yl)-2-methoxyiminoacetamido]-3-[6-methyl-5-(1H-imidazo[1,2-b]pyrazolio)]methyl-3-cephem-4-carboxylate (syn isomer)

IR (Nujol): 1760, 1680, 1600 cm$^{-1}$.

NMR (D$_2$O-NaHCO$_3$, δ): 2.50 (3H, s), 3.00 and 3.33 (2H, ABq, J=18Hz), 3.98 (3H, s), 5.16 (1H, d, J=5Hz), 5.25 (2H, br s), 5.79 (1H, d, J=5Hz), 6.20 (1H, br s), 6.88 (1H, s), 7.35 (1H, d, J=2Hz), 7.61 (1H, d, J=2Hz).

EXAMPLE 4

To a solution of 7β-[2-(2-aminothiazol-4-yl)-2-methoxyiminoacetamido]-3-[5-(1H-imidazo[1,2-b]pyrazolio)]-methyl-3-cephem-4-carboxylate (syn isomer) in water (0.2 ml) were added 2M sulfuric acid (0.2 ml) and ethanol (0.2 ml). The mixture was stirred at room temperature for 1 hour. The insoluble material was filtered off and the filtrate was concentrated to remove ethanol and lyophilized to give 7β-[2-(2-aminothiazol-4-yl)-2-methoxyiminoacetamido]-3-[5-(1H-imidazo[1,2-b]pyrazolio)]-methyl-3-cephem-4-carboxylate sulfate (syn isomer) (0.15 g).

IR (Nujol): 1770, 1670, 1610 cm$^{-1}$.

NMR (D$_2$O-NaHCO$_3$, δ): 3.11 and 3.40 (2H, ABq, J=18Hz), 3.97 (3H, s), 5.16 (1H, d, J=5Hz), 5.28 (2H, br s), 5.78 (1H, d, J=5Hz), 6.41 (1H, d, J=3Hz), 6.93 (1H, s), 7.45 (1H, d, J=2Hz), 7.87 (1H, d, J=2Hz), 7.98 (1H, d, J=3Hz).

PREPARATION 11

To a suspension of ethyl ethoxymethylenecyanoacetate (21.7 g) in ethanol (65 ml) was added dropwise a solution of hydrazinoacetaldehyde diethyl acetal (19 g) in water (19 ml) under ice-cooling. The mixture was stirred at 80° C. for 1.5 hours and evaporated to remove ethanol. To the residue was 4N sodium hydroxide (64 ml), and the mixture was refluxed for 1 hour. The mixture was adjusted to pH 3.5 with concentrated hydrochloric acid at 10°-20° C., and the resulting precipitate was collected by filtration to give 1-(2,2-diethoxyethyl)-4-carboxy-5-aminopyrazole (8.60 g).

IR (Nujol) : 3460, 3360, 1645, 1620, 1545 cm$^{-1}$.

NMR (DMSO-d$_6$, δ): 1.05 (6H, :, T=7Hz), 3.41 (2H, q, J=7Hz), 3.63 (2H, q, J=7Hz), ...  (2H, d, J=5.5Hz), 4.80 (1H, t, J=5.5Hz), 6.14 (2H, br s,, .'' (1H, s)

PREPARATION 12

To a solution of 1-[2,2-diethoxyethyl)-4-carboxy-5-aminopyrazole (1 g) in tetrahydrofuran (20 ml) was added 4N hydrochloric acid (10 ml), and the solution was refluxed for 1 hour. The mixture was adjusted to pH 8 with 5N sodium hydroxide (10 ml) and extracted with a mixture of tetrahydrofuran and ethyl acetate. The organic layer was dried over magnesium sulfate and evaporated in vacuo to give 1H-imidazo[1,2-b]pyrazole (235 mg)

NMR (DMSO-$d_6$, δ): 5.62 (1H, d, J=2Hz), 7.14 (1H, br s), 7.45 (1H, d, J=2Hz), 7.49 (1H, br s), 10.97 (1H, br s).

PREPARATION 13

To a suspension of 62% sodium hydride (0.36 g) in N,N-dimethylformamide (6 ml) was added 1H-imidazo[1,2-b]-pyrazole (1 g) under ice-cooling Then, thereto was added dropwise methyl iodide (0.58 ml) at the same temperature After the mixture was stirred at room temperature for 4 hours, ethyl acetate was added thereto The precipitate was filtered off, and the organic solvent was evaporated in vacuo. The residue was purified by column chromatography on silica gel to give 1-methyl-1H-imidazo-[1,2-b]pyrazole (0.9 g).

IR (Neat) 1590, 1550 cm$^{-1}$.

NMR (DMSO-$d_6$, δ): 3.57 (3H, s), 5.65 (1H, m), 7.09 (1H, m), 7.46 (2H, m).

PREPARATION 14

To a suspension of 5-amino-4-carboxy-1-(2,2-diethoxyethyl)pyrazole (4 g) in xylene (15.6 ml) was added dropwise 3.4M solution of sodium bis(2-methoxyethoxy)-aluminum hydride in toluene (15.6 ml) at room temperature in an atmosphere of nitrogen. Then the mixture was refluxed for 6 hours, and poured into a mixture of dichloromethane and water. The precipitate was filtered off, and the organic layer was separated and dried over magnesium sulfate. The organic solvent was evaporated in vacuo to give 5-amino-4-methyl-1-[(E)-2-ethoxyvinyl]-pyrazole (598 mg).

IR (Nujol): 3440, 3280, 3150, 1665, 1625, 1585, 1520 cm$^{-1}$.

NMR (DMSO-$d_6$, δ): 1.23 (3H, t, J=7Hz), 1.79 (3H, s), 3.79 (2H, q, J=7Hz), 5.05 (2H, br s), 6.63 (1H, d, J=11Hz), 6.95 (1H, s), 7.00 (1H, d, J=11Hz).

PREPARATION 15

To a solution of 5-amino-4-methyl-1-[(E)-2-ethoxyvinyl]pyrazole (10.6 g) in tetrahydrofuran (212 ml) was added 4N hydrochloric acid, and the mixture was refluxed for 3 hours. The reaction mixture was adjusted to pH 8 under ice-cooling, thereto was added ethyl acetate (100 ml). The separated organic layer was dried over magnesium sulfate and evaporated in vacuo to give 7-methyl-1H-imidazo[1,2-b]pyrazole (6.92 g) as crystals.

IR (Nujol) 3100, 1620, 1500 cm$^{-1}$.

NMR (DMSO-$d_6$, δ): 2.08 (3H, s), 7.10 (1H, m), 7.25 (1H, s), 7.40 (1H, m), 10.89 (1H, br s).

PREPARATION 16

The following compound was obtained according to a similar manner to that of preparation 3.

1-Formyl-7-methyl-1H-imidazo[1,2-b]pyrazole

IR (Nujol): 3100, 1705, 1610, 1560 cm$^{-1}$.

NMR (DMSO-$d_6$, δ): 2.33 (3H, s), 7.49 (1H, s), 7.65 (1H, m), 7.80 (1H, m), 8.89 (1H, s).

PREPARATION 17

A mixture of 2-bromopropionaldehyde diethyl acetal (71 g) and hydrazin anhydride (43 ml) was dissolved in ethanol (284 ml). The solution was refluxed for 24 hours. The reaction mixture was evaporated to remove ethanol. The residue was dissolved in aqueous 2N-sodium hydroxide (170 ml) and extracted with diethyl ether (500 ml×3). The organic layer was dried over magnesium sulfate and the solvent was distilled off in vacuo to give 2-hydrazinopropionaldehyde diethyl acetal (54.4 g).

NMR (DMSO-$d_6$, δ): 0.93 (3H, d, J=6Hz), 1.06-1.17 (6H, m), 2.65 (1H, q, J=6Hz), 3.37-3.71 (4H, m), 4.26 (1H, d, J=6Hz).

PREPARATION 18

To a solution of 2-(ethoxymethylene)-2-cyanoacetic acid ethyl ester (56.3 g) in ethanol (200 ml) was added dropwise 2-hydrazinopropionaldehyde diethyl acetal (54 g) in ethanol (80 ml) at room temperature. The mixture was refluxed for 4 hours. The reaction mixture was cooled at room temperature and the solvent was distilled off in vacuo to give the crude. 1-(1-methyl-2,2-diethoxyethyl)-4-ethoxycarbonyl-5-aminopyrazole (100 g). The crude product (100 g) was dissolved in aqueous 4N-sodium hydroxide (170 ml) and the mixture was refluxed for 1 hour. The reaction mixture was cooled at room temperature and washed with ethyl acetate (100 ml×2). The aqueous solution was adjusted to pH 3.5 with 6N-hydrochloric acid and stirred for 1 hour. The precipitate was collected by filtration, washed with water and dried over phosphorus pentoxide to give 1-(1-methyl-2,2-diethoxyethyl)-4-carboxy-5-aminopyrazole (9.93 g).

IR (Nujol) : 3450, 3350, 1680, 1620, 1540 cm$^{-1}$.

NMR (DMSO-$d_6$, δ): 0.90 (3H, t, J=7Hz), 1.15 (3H, t, J=7Hz), 1.30 (3H, d, J=7Hz), 3.12-3.70 (4H, m), 4.25-4.39 (1H, m), 4.62 (1H, d, J=7Hz), 6.17 (2H, br s), 7.45 (1H, s)

PREPARATION 19

1-(1-Methyl-2,2-diethoxyethyl)-4-carboxy-5-aminopyrazole (9.9 g) was dissolved in tetrahydrofuran (200 ml) and thereto was added 3N-hydrochloric acid (52 ml). The mixture was refluxed for 3 hours. The reaction mixture was cooled at room temperature, adjusted to pH 6 with aqueous 30% potassium carbonate and extracted with ethyl acetate (100 ml). Further the separated aqueous layer was extracted with ethyl acetate (50 ml). The organic layer was combined and dried over magnesium sulfate. The solvent was distilled off in vacuo. The residue was pulverized with isopropyl ether and the powder was collected by filtration to give 3-methyl-1H-imidazo[1,2-b]pyrazole (3.01 g).

IR (Nujol) : 3450, 1600 cm$^{-1}$.

NMR (DMSO-$d_6$, δ) : 2.29 (3H, s), 5.60 (1H, d, J=2Hz), 6.86 (1H, s), 7.45 (1H, d, J=2Hz).

PREPARATION 20

A mixture of acetic anhydride (4.83 ml) and formic acid (3.86 ml) was stirred at room temperature for 1 hour. The solution was cooled at ice-bath and 3-m... 1H-imidazo[1,2-b]pyrazole (3.1 g) was added thereto. The mixture was stirred at the same condition for 1 hour. The reaction mixture was evaporated and the residue was subjected to column chromatography on silica gel using ethyl acetate as an eluent. Fractions containing the object compound were combined and the solvent was evaporated to give 1-formyl-3-methyl-1H-imidazo[1,2-b]pyrazole (2.99 g).

IR (Nujol) : 1700, 1560 cm$^{-1}$.

NMR (DMSO-d$_6$, δ) : 2.37 (3H, s), 6.27 (1H, br s), 7.46 (1H, br s), 7.70 (1H, br s), 8.95 (1H, s).

PREPARATION 21

To a suspension of 62% sodium hydride (7.23 g) in N,N-dimethylformamide (70 ml) was added 1H-imidazo[1,2-b]-pyrazole (20 g) by portions under ice-cooling. A solution of ethyl bromoacetate (20.7 ml) in N,N-dimethylformamide (50 ml) was added thereto at the same condition. The mixture was stirred for 2 hours at room temperature. The reaction mixture was poured into a mixture of ethyl acetate (1 l) and water (500 ml). The separated organic layer was washed with water and brine, and dried over magnesium sulfate. The solvent was evaporated and the residue was subjected to column chromatography on silica gel using ethyl acetate as an eluent. Fractions containing the object compound were combined and evaporated in vacuo to give 1-ethoxycarbonylmethyl-1H-imidazo[1,2-b]pyrazole (25 g).

NMR (DMSO-d$_6$, δ): 1.21 (3H, t, J=7Hz), 4.15 (2H, q, J=7Hz), 4.89 (2H, s), 5.69 (1H, d, J=2Hz), 7.15 (1H, d, J=3Hz), 7.46 (1H, d, J=3Hz), 7.54 (1H, d, J=2Hz).

PREPARATION 22

To a suspension of lithium aluminum hydride (1.57 g) in tetrahydrofuran (80 ml) was dropwise added a solution of 1-ethoxycarbonylmethyl-1H-imidazo[1,2-b]pyrazole (8 g) in tetrahydrofuran (40 ml) at 50° C. The mixture was refluxed for 1 hour. The reaction mixture was cooled under ice-bath. To a cooled mixture was added sodium fluoride (6.95 g) and then water (2.23 ml) was added thereto under ice-cooling. The insoluble material was filtered off and the filtrate was evaporated to give the crystals. The crystals were washed with isopropyl ether and dried to give 1-(2-hydroxyethyl)-1H-imidazo[1,2-b]-pyrazole (4.82 g).

IR (Nujol): 1720, 1600 cm$^{-1}$.

NMR (DMSO-d$_6$, δ): 3.70 (2H, q, J=5Hz), 3.94 (2H, t, J=5Hz), 4.93 (1H, t, J=5Hz), 5.69 (1H, d, J=2Hz), 7.14 (1H, d, J=3Hz), 7.45 (1H, d, J=3Hz), 7.49 (1H, d, J=2Hz).

PREPARATION 23

The following compounds were obtained according to a similar manner to that of Preparation 5.

(1) Benzhydryl 7β-t-butoxycarbonylamino-3-[1-methyl-5-(1H-imidazo[1,2-b]pyrazolio)]methyl-3-cephem-4-carboxylate iodide IR (Nujol) : 1780, 1720, 1605 cm$^{-1}$.

NMR (DMSO-d$_6$, δ) : 1.42 (9H, s), 3.33 (2H, br s), 3.82 (3H, s), 5.12 and 5.33 (2H, ABq, J=15Hz), 5.15 (1H, d, J=5Hz), 5.61 (1H, dd, J=8Hz, 5Hz), 6.69 (1H, d, J=3Hz), 6.96 (1H, s), 7.17–7.51 (10H, m), 7.71 (1H, m) 7.79 (1H, m), 7.95 (1H, d, J=8Hz), 8.15 (1H, m).

(2) Benzhydryl 7β-t-butoxycarbonylamino-3-[1-(2-hydroxyethyl)-5-(1H-imidazo[1,2-b]pyrazolio)]methyl-3-cephem.-4-carboxylate iodide NMR (DMSO-d$_6$,δ): 1.40 (9H, s), 3.42 (2H, br s), 3.75 (2H, q, J=5Hz), 4.12 (2H, t, J=5Hz), 5.04 (1H, t, J=5Hz), 5.17 (1H, d, J=5Hz), 5.28 and 5.45 (2H, ABq, J=16Hz), 5.65 (1H, dd, J=5, 8Hz), 6.69 (1H, d, J=3Hz), 6.96 (1H, s), 7.26–7.51 (10H, m), 7.76 (1H, br s), 7.84 (1H, br s), 8.07 (1H, d, J=8Hz), 8.13 (1H, d, J=3Hz).

PREPARATION 24

To a suspension of benzhydryl 7β-t-butoxyoarbonylamino-3-chloromethyl-3-cephem-4-carboxylate (25.4 g) and sodium iodide (7.4 g) in N,N-dimethylformamide (25 ml) was added 1-formyl-1H-imidazo[1,2-b]pyrazole (10 g) at room temperature. After being stirred for 20 hours at the same temperature, the mixture was poured into a mixture of ethyl acetate and ice-water. The separated organic layer was washed with water and brine, and dried over magnesium sulfate. The organic solvent was evaporated in vacuo to give benzhydryl 7β-t-butoxycarbonylamino-3-[5-(1H-imidazo[1,2-b]pyrazolio)]methyl-3-cephem-4-carboxylate iodide (31.1 g).

NMR (DMSO-d$_6$, δ) : 1.41 (9H, s), 3.43 (2H, br s), 5.17 (1H, d, J=5Hz), 5.38 (2H, m), 5.61 (1H, dd, J=8Hz, 5Hz), 6.58 (1H, d, J=3Hz), 6.97 (1H, s), 7.15–7.53 (10H, m), 7.70 (1H, m), 7.79 (1H, m), 7.97 (1H, d, J=8Hz), 8.15 (1H, m).

PREPARATION 25

To a solution of benzhydryl 7β-t-butoxycarbonylamino-3-chloromethyl-3-cephem-4-carboxylate (6.2 g) in N,N-dimethylformamide (6 ml) was added sodium iodide (1.8 g). After the mixture was stirred at room temperature for 30 minutes. Thereto was added 1-formyl-3-methyl-1H-imidazo[1,2-b]pyrazole (2.9 g). The mixture was stirred at the same condition for 30 hours. The reaction mixture was poured into a mixture of ethyl acetate (180 ml) and water (120 ml). The separated organic layer was washed with water and then brine, and dried over magnesium sulfate. The solvent was evaporated in vacuo and the residue was pulverized with isopropyl ether and collected by filtration to give benzhydryl 7β-t-butoxycarbonylamino-3-[3-methyl-5-(1H-imidazo[1,2-b]pyrazolio)]methyl-3-cephem-4-carboxylate iodide (4.66 g).

IR (Nujol) : 1780, 1610 cm$^{-1}$.

NMR (DMSO-d$_6$, δ): 1.41 (9H, s), 2.31 (3H, s), 3.30 and 3.45 (2H, ABq, J=18Hz), 5.16 (1H, d, J=5Hz), 5.36 and 5.57 (2H, ABq, J=16Hz), 5.57–5.66 (1H, m), 6.53 (1H, d, J=3Hz), 6.95 (1H, s), 7.00–7.50 (11H, m), 8.18 (1H, d, J=3Hz).

PREPARATION 26

The following compound was obtained according to similar manners to those of Preparation 24 and Preparation 25.

Benzhydryl 7β-t-butoxycarbonylamino-3-[7-methyl-5-(1H-imidazo[1,2-b]pyrazolio)]methyl-3-cephem-4-carboxylate iodide IR (Nujol) : 3280, 1790, 1715, 1680 cm$^{-1}$.

NMR (DMSO-d$_6$, δ): 1.41 (9H, s), 2.17 (3H, s), 3.40 (2H, br s), 5.11 and 5.36 (2H, ABq, J=15Hz), 5.13 (1H, d, J=5Hz), 5.58 (1H, dd, J=8Hz, 5Hz), 6.92 (1H, s), 7.08–7.46 (10H, m), 7.67 (1H, m), 7.77 (1H, m), 7.85 (1H, m), 7.92 (1H, d, J=8Hz).

PREPARATION 27

To a suspension of benzhydryl 7β-t-butoxycarbonylamino-3-[3-methyl-5-(1H-imidazo[1,2-b]-pyrazolio)]methyl-3-cephem-4-carboxylate iodide (4.6 g) in a mixture of anisole (4.6 ml) and dichloromethane (14 ml) was added dropwise trifluoroacetic acid (9.2 ml) under ice-cooling. The mixture was stirred at room temperature for 2 hours. The reaction mixture was poured into a mixture of isopropyl ether (140 ml) and ethyl acetate (140 ml). The resultant powder was collected by filtration and washed with isopropyl ether and dried over phosphorus pentoxide in vacuo to give 7β-amino-3-[3-methyl-5-(1H-imidazo[1,2-b]pyrazolio)]methyl-3-cephem-4-carboxylate bis(trifluoroacetate) (2.75 g).

IR (Nujol): 1780, 1660, 1590 cm$^{-1}$.

PREPARATION 28

The following compound were obtained according to a similar manner to that of Preparation 27.

(1)
7β-Amino-3-[1-methyl-5-(1H-imidazo[1,2-b]pyrazolio)]-methyl-3-cephem-4-carboxylate bis(trifluoroacetate)

IR (Nujol) : 1780, 1660, 1600 cm$^{-1}$.

NMR (D$_2$O, δ) : 3.28 and 3.55 (2H, ABq, J=18Hz), 3.83 (3H, s), 5.18 (1H, d, J=5Hz), 5.29 (1H, d, J=5Hz), 5.41 (2H, br s), 6.25 (1H, d, J=3Hz), 7.43 (1H, m), 7.87 (1H, m), 8.04 (1H, d, J=3Hz)

(2)
7β-Amino-3-[7-methyl-5-(1H-imidazo[1,2-b]pyrazolio)]-methyl-3-cephem-4-carboxylate bis(trifluoroacetate)

IR (Nujol) : 1780, 1670, 1610 cm$^{-1}$.

NMR (D$_2$O, δ) : 2.20 (3H, s), 3.37 and 3.53 (2H, ABq, J=18Hz), 5.24 (2H, s), 5.41 (2H, s), 7.79 (1H, s), 8.06 (2H, m).

(3)
7β-Amino-3-[1-(2-hydroxyethyl)-5-(1H-imidazo[1,2-b]pyrazolio)methyl-3-cephem-4-carboxylate bis(trifluoroacetate)

IR (Nujol) : 1780, 1670, 1590 cm$^{-1}$.

NMR (DMSO-d$_6$, δ): 3.35 and 3.54 (2H, ABq, J=18Hz), 3.76 (2H, q, J=5Hz), 4.22 (2H, t, J=5Hz), 4.70 (1H, t, J=5Hz), 5.21 (2H, br s), 5.47 (2H, br s), 6.73 (1H, d, J=3Hz), 7.82 (1H, br s), 8.12 (1H, br s), 8.27 (1H, d, J=3Hz)

PREPARATION 29

To a solution of benzhydryl 7β-t-butoxycarbonylamino-3-[5-(1H-imidazo[1,2-b]pyrazolio)]methyl-3-cephem-4-carboxylate iodide (31 g) in formic acid (124 ml) was added conc. hydrochloric acid (7.67 ml) at room temperature. After being stirred for 2 hours at the same temperature, the mixture was poured into a mixture of acetone (1 l) and ethyl acetate (2 l). The resulting precipitate was collected by filtration to give 7β-amino-3-[5-{1H-imidazo[1,2-b]pyrazolio)]methyl-3-cephem-4-carboxylate dihydrochloride hydroiodide (17.39 g).

NMR (D$_2$O, δ) : 3.30 and 3.59 (2H, ABq, J=18Hz), 5.21 (1H, d, J=5Hz), 5.32 (1H, d, J=5Hz), 5.48 (2H, br s), 6.48 (1H, d, J=3Hz), 7.50 (1H, m), 7.88 (1H, m), 8.06 (1H, m).

PREPARATION 30

A solution of 7β-amino-3-[5-(1H-imidazo[1,2-b]-pyrazolio)]methyl-3-cephem-4-carboxylate dihydrochloride hydroiodide (15.3 g) in water (61.2 ml) was subjected to column chromatography on Diaion HP 20 (107.1 ml) and eluted with water. The desired fractions (120 ml) was obtained and isopropyl alcohol (500 ml) was added thereto under ice-cooling. The mixture was stirred for 2 hours at the same temperature, and the resulting precipitate was collected by filtration to give 7β-amino-3-[(5-(1H-imidazo[1,2-b]pyrazolio)]methyl-3-cephem-4-carboxylate hydrochloride (7.0 g) as crystals.

IR (Nujol) : 3550, 3390, 1780, 1650, 1605 cm$^{-1}$.

NMR (D$_2$O, δ): 3.26 and 3.50 (2H, ABq, J=18Hz), 5.16 (1H, d, J=5Hz), 5.26 (1H, d, J=5Hz), 5.35 (2H, br s), 6.47 (1H, d, J=3Hz), 7.51 (1H, m), 7.90 (1H, m), 8.05 (1H, m)

EXAMPLE 5

To a solution of a mixture of 7β-amino-3-[1-(2-hydroxyethyl)-5-(1H-imidazo[1,2-b]pyrazolio)]methyl-3-cephem-4-carboxylate bis(trifluoroacetate) (1.2 g) and N-trimethylsilylacetamide (2.66 g) in tetrahydrofuran (24 ml) was added 2-(2-aminothiazol-4-yl)-2-methoxyiminoacetyl chloride hydrochloride (syn isomer) (0.62 g) under ice-cooling. The mixture was stirred for 2 hours at the same condition. The reaction mixture was poured into ethyl acetate (240 ml). The resultant precipitate was collected by filtration, washed with isopropyl ether and dried over phosphorus pentoxide in vacuo. The crude product was dissolved in water and adjusted to pH 2.5 with 1N-hydrochloric acid. The aqueous solution was subjected to column chromatography on Diaion HP-20 using aqueous 10% isopropyl alcohol as an eluent. Fractions containing the object compound were combined and evaporated in vacuo to remove isopropyl alcohol and lyophilized to give 7β-[2-(2-aminothiazol-4-yl)-2-methoxyiminoacetamido]-3-[1-(2-hydroxyethyl)-5-(1H-imidazo[1,2-b]pyrazolio)]methyl-3-cephem-4-carboxylate (syn isomer) (0.50 g).

IR (Nujol) : 1760, 1660, 1600 cm$^{-1}$.

NMR (D$_2$O, δ) : 3.13 and 3.44 (2H, ABq, J=18Hz), 3.97 (3H, s), 3.85–4.10 (2H, m), 4.27 (2H, t, J=5Hz), 5.17 (1H, d, J=5Hz), 5.29 (2H, br s), 5.78 (1H, d, J=5Hz), 6.48 (1H, d, J=3Hz), 6.90 (1H, s), 7.47 (1H, br s), 7.93 (1H, br s), 8.01 (1H, d, J=3Hz).

EXAMPLE 6

The following compounds were obtained according to similar manners to those of Examples 1, 2 and 5.

(1)
7β-[2-(2-Aminothiazol-4-yl)-2-ethoxyiminoacetamido]-3-[5-(1H-imidazo[1,2-b]pyrazolio)]methyl-3-cephem-4-carboxylate (syn isomer)

IR (Nujol) : 1770, 1665, 1610, 1520 cm$^{-1}$.

NMR (DMSO-d$_6$, δ): 1.20 (3H, t, J=7Hz), ... rd, 3.35 (2H, ABq, J=18Hz), 4.05 (2H, q, J=7Hz), 5.05 (1H, d, J=5Hz), 5.20-5.50 (2H, m), 5.66 (1H, dd, J=5Hz, 8Hz), 6.45 (1H, d, J=5Hz), 6.68 (1H, s), 7.15 (2H, br s), 7.49-7.62 (1H, m), 8.18 (1H, d, J=5Hz), 8.38-8.55 (1H, m), 9.46 (1H, d, J=8Hz).

(2)

7β-[2-(2-Aminothiazol-4-yl)-2-allyloxyimino-acetamido]-3-[5-(1H-imidazo[1,2-b]pyrazolio)]methyl-3-cephem-4-carboxylate (syn isomer)

IR (Nujol): 1770, 1665, 1610, 1530 cm$^{-1}$.

NMR (DMSO-d$_6$, δ): 2.90 and 3.35 (2H, ABq, J=18Hz), 4.36–4.70 (2H, m), 5.05 (1H, d, J=5Hz), 5.10–5.48 (2H, m), 5.63 (1H, dd, J=5Hz, 8Hz), 5.60–6.15 (1H, m), 6.46 (1H, d, J=3Hz), 6.68 (1H, s), 7.16 (2H, br s), 7.48–7.63 (1H, m), 8.18 (1H, d, J=3Hz), 8.35–8.55 (1H, m), 9.55 (1H, d, J=8Hz).

(3)

7β-[2-(2-Aminothiazol-4-yl)-2-ethoxyiminoacetamido]-3-[1-methyl-5-(1H-imidazo[1,2-b]pyrazolio)]methyl-3-cephem-4-carboxylate (syn isomer)

IR (Nujol): 1770, 1660, 1625, 1605, 1525 cm$^{-1}$.

NMR (D$_2$O +NaHCO$_3$, δ): 1.30 (3H, t, J=7Hz), 3.15 and 3.43 (2H, ABq, J=18Hz), 3.83 (3H, s), 4.26 (2H, q, J=7Hz), 5.20 (1H, d, J=5Hz), 5.28 (2H, br s), 5.80 (1H, d, J=5Hz), 6.46 (1H, d, J3Hz), 6.90 (1H, s), 7.25–7.46 (1H, m), 7.86 (1H, d, J=3Hz), 7.93–8.06 (1H, m)

(4)

7β-[2-(2-Aminothiazol-4-yl)-2-allyloxyimino-acetamido]-3-[1-methyl-5-(1H-imidazo[1,2-b]pyrazolio)]-methyl-3-cephem-4-carboxylate (syn isomer)

IR (Nujol): 1765, 1660, 1620, 1595, 1525 cm$^{-1}$.

NMR D$_2$O, δ): 3.13 and 3.45 (2H, ABq, J=18Hz), 3.90 (3H, s), 5.05–5.20 (2H, m), 5.23 (1H, d, J=5Hz), 5.30–5.58 (2H, m), 5.80 (1H, d, J=5Hz), 5.85–6.33 (1H, m), 6.43 (1H, d, J=3Hz), 6.96 (1H, s), 7.30–7.50 (1H, m), 7.80–7.91 (1H, m), 8.01 (1H, d, J=3Hz)

(5)

7β-[2-(5-Amino-1,2,4-thiadiazol-3-yl)-2-ethoxy-iminoacetamido]-3-[5-(1H-imidazo[1,2-b]pyrazolio)-methyl-3-cephem-4-carboxylate (syn isomer)

IR (Nujol): 3300, 1760, 1660, 1600 cm$^{-1}$.

NMR (D$_2$O, δ): 1.30 (3H, t, J=7Hz), 3.11 and 3.39 (2H, ABq, J=18Hz), 4.33 (2H, q, J=7Hz), 5.18 (1H, d, J=5Hz), 5.28 (2H, br s), 5.83 (1H, d, J=5Hz), 6.38 (1H, d, J=3Hz), 7.43 (1H, m), 7.87 (1H, m), 7.98 (1H, d, J=3Hz)

(6)

7β-[2-(5-Amino-1,2,4-thiadiazol-3-yl)-2-(1-carboxy-1-methylethoxyiminoacetamido]-3-[5-(1H-imidazo[1,2-b]pyrazolio)]methyl-3-cephem-4-carboxylate (syn isomer)

IR (Nujol): 3120, 1765, 1660, 1620 cm$^{-1}$.

NMR (D$_2$O+NaHCO$_3$, δ): 1.50 (6H, s), 3.19 and 3.39 (2H, ABq, J=18Hz), 5.18 (1H, d, J=5Hz), 5.28 (2H, br s), 5.82 (1H, d, J=5Hz), 6.39 (1H, d, J=3Hz), 7.43 (1H, m), 7.88 (1H, m), 7.98 (1H, d, J=3Hz)

(7)

7β-[2-(5-Amino-1,2,4-thiadiazol-3-yl)-2-allyloxyimino-acetamido]-3-[5-(1H-imidazo[1,2-b]pyrazolio)methyl-3-cephem-4-carboxylate (syn isomer)

IR (Nujol): 3300, 3120, 1760, 1660, 1600 cm$^{-1}$.

NMR (D$_2$O+DCl, δ): 3.28 and 3.63 (2H, ABq, J=18Hz), 4.92 (2H, m), 5.19 and 5.63 (2H, ABq, J=15Hz), 5.29 (1H, d, J=5Hz), 5.31–6.21 (3H, m), 5.91 (1H, d, J=5Hz), 6.51 (1H, d, J=3Hz), 7.53 (1H, m), 7.89 (1H, m), 8.07 (1H, m).

(8)

7β-[2-(5-Amino-1,2,4-thiadiazol-3-yl)-2-methoxy-iminoacetamido]-3-[1-methyl-5-(1H-imidazo[1,2-b]-pyrazolio)]methyl-3-cephem-4-carboxylate (syn isomer)

IR (Nujol): 1760, 1670, 1595 cm$^{-1}$.

NMR (D$_2$O+DCl, δ): 3.08 and 3.43 (2H, ABq, J=18Hz), 3.64 (3H, s), 3.91 (3H, s), 5.08 (1H, d, J=5Hz), 5.11 and 5.38 (2H, ABq, J=15Hz), 5.64 (1H, d, J=5Hz), 6.34 (1H, d, J=3Hz), 7.25 (1H, m), 7.65 (1H, m), 7.86 (1H, d, J=3Hz).

(9)

7β-[2-(2-Aminothiazol-4-yl)-2-methox-yiminoacetamido]-3-[1-methyl-5-(1H-imidazo[1,2-b]pyrazolio)]methyl-3-cephem-4-carboxylate (syn isomer)

IR (Nujol): 1765, 1660, 1605 cm$^{-1}$.

NMR (D$_2$O, δ): 3.11 and 3.45 (2H, ABq, J=18Hz), 3.82 (3H, s), 3.98 (3H, s), 5.19 (1H, d, J=5Hz), 5.28 (2H, br s), 5.78 (1H, d, J=5Hz), 6.48 (1H, d, J=3Hz), 6.90 (1H, s), 7.40 (1H, m), 8.02 (1H, d, J=3Hz).

(10)

7β-[2-(5-Amino-1,2,4-thiadiazol-3-yl)-2-(1-carboxy-1-methylethoxyimino)acetamido]-3-[1-methyl-5-(1H-imidazo-[1,2-b]pyrazolio)]methyl-3-cephem-4-carboxy-late (syn isomer)

IR (Nujol): 3300, 1765, 1665, 1600 cm$^{-1}$.

NMR (D$_2$O+NaHCO$_3$, δ): 1.48 (6H, s), 3.08 and 3.39 (2H, ABq, J=18Hz), 3.79 (3H, s), 5.17 (1H, d, J=5Hz), 5.25 (2H, br s), 5.80 (1H, d, J=5Hz), 6.45 (1H, d, J=3Hz), 7.38 (1H, m), 7.87 (1H, m), 7.98 (1H, d, J=3Hz).

(11)

7β-[2-[5-Amino-1,2,4-thiadiazol-3-yl)-2-ethoxyimino-acetamido]-3-[1-methyl-5-(1H-imidazo[1,2-b]pyrazolio)]-methyl-3-cephem-4-carboxylate (syn isomer)

IR (Nujol): 3270, 1760, 1660, 1595 cm$^{-1}$.

NMR (D$_2$O +DCl, δ): 1.33 (3H, t, J=7Hz), 3.29 and 3.65 (2H, ABq, J=18Hz), 3.86 (3H, s), 4.43 (2H, q, J=7Hz), 5.32 (1H, d, J=5Hz), 5.35 and 5.62 (2H, ABq, J=15Hz), 5.86 (1H, d, J=5Hz), 6.55 (1H, d, J=3Hz), 7.46 (1H, d, J=2Hz), 7.86 (1H, d, J=2Hz), 8.08 (1H, d, J=3Hz).

(12)

7β-[2-(5-Amino-1,2,4-thiadiazol-3-yl)-2-allyloxy-iminoacetamido]-3-[1-methyl-5-(1H-imidazo[1,2-b]-pyrazolio)]methyl-3-cephem-4-carboxylate (syn isomer)

IR (Nujol): 3120, 1770, 1670, 1605 cm$^{-1}$.

NMR (D$_2$O, δ): 3.27 and 3.63 (2H, ABq, J=18Hz), 3.87 (3H, s), 4.88 (2H, br s), 5.18–5.67 (2H, m), 5.28 (1H, d, J=5Hz), 5.33 and 5.59 (2H, ABq, J=15Hz), 5.87 (1H, d, J=5Hz), 5.91–6.25 (1H, m), 6.53 (1H, d, J=3Hz), 7.43 (1H, m), 7.84 (1H, m), 8.03 (1H, d, J=3Hz).

(13)

7β-[2-(5-Amino-1,2,4-thiadiazol-3-yl)-2-methoxy-iminoacetamido]-3-[7-methyl-5-(1H-imidazo[1,2-b]-pyrazolio)]methyl-3-cephem-4-carboxylate (syn isomer)

IR (Nujol): 3300, 1760, 1665, 1605 cm$^{-1}$.

NMR (D$_2$O, δ): 2.24 (3H, s), 3.27 and 3.60 (2H, ABq, J=18Hz), 4.10 (3H, s), 5.24 and 5.52 (2H, ABq, J=15Hz), 5.28 (1H, d, J=5Hz), 5.88 (1H, d, J=5Hz), 7.47 (1H, m), 7.79 (2H, m).

(14) 7β-[2-(2-Aminothiazol-4-yl)-2-methoxyiminoacetamido]-3-[7-methyl-5-[7-methyl-5-(1H-imidazo[1,2-b]pyrazolio)]methyl-3cephem-4-carboxylate (syn isomer)

IR (Nujol): 3300, 1770, 1670, 1610 cm$^{-1}$.
NMR D$_2$O, δ): 1.26 (3H, s), 3.29 and 3.61 (2H, ABq, J=18Hz), 4.08 (3H, s), 5.28 (1H, d, J=5Hz), 5.29 and 5.53 (2H, ABq, J=15Hz), 5.82 (1H, d, J=5Hz), 7.12 (1H, s), 7.48 (1H, m), 7.80 (2H, m).

(15) 7β-[2-(5-Amino-1,2,4-thiadiazol-3-yl)-2-methoxyiminoacetamido]-3-[3-methyl-5-(1H-imidazo[1,2-b]pyrazolio)]-methyl-3-cephem-4-carboxylate (syn isomer)

IR (Nujol): 1770, 1670, 1610 cm$^{-1}$.
NMR [D$_2$O, δ): 2.54 (3H, s), 3.27 [2H, br s), 4.05 (3H, s), 5.17 (1H, d, J=5Hz), 5.18 and 5.57 (2H, ABq, J=15Hz), 5.84 (1H, d, J=5Hz), 6.33 (1H, d, J=3Hz), 7.10 (1H, br s), 7.88 (1H, d, J=3Hz).

(16) 7β-[2-(2-Aminothiazol-4-yl)-2-methoxyiminoacetamido]-3-[3-methyl-5-(1H-imidazo[1,2-b]pyrazolio)]methyl-3-cephem-4-carboxylate (syn isomer)

IR (Nujol): 1760, 1660, 1600 cm$^{-1}$.
NMR (D$_2$O, δ): 2.57 (3H, s), 3.27 (2H, br s), 3.98 (3H, s), 5.17 (1H, d, J=5Hz), 5.18 and 5.57 (2H, ABq, J=15Hz), 5.80 (1H, d, J=5Hz), 6.33 (1H, d, J=3Hz), 6.92 (1H, s), 7.09 (1H, br s), 7.88 (1H, d, J=3Hz).

(17) 7β-[2-(5-Amino-1,2,4-thiadiazol-3-yl)-2-methoxyiminoacetamido]-3-[1-(2-hydroxyethyl)-5-(1H-imidazo[1,2-b]pyrazolio)]methyl-3-cephem-4-carboxylate (syn isomer)

IR (Nujol): 1760, 1660, 1590 cm$^{-1}$.
NMR (D$_2$O, δ): 3.15 and 3.44 (2H, ABq, J=18Hz), 3.95 (2H, t, J=5Hz), 4.29 (2H, t, J=5Hz), 5.17 (1H, d, J=5Hz), 5.30 (1H, br s), 5.82 (1H, d, J=5Hz), 6.49 (1H, d, J=3Hz), 7.48 (1H, d, J=2Hz), 7.92 (1H, d, J=2Hz), 8.02 (1H, d, J=3Hz).

(18) 7β-[2-(5-Amino-1,2,4-thiadiazol-3-yl)-2-ethoxyiminoacetamido]-3-[1-(2-hydroxyethyl)-5-(1H-imidazo-[1,2-b]pyrazolio)]methyl-3-cephem-4-carboxylate (syn isomer)

IR (Nujol): 1760, 1660, 1500 cm$^{-1}$.
NMR (D$_2$O, δ): 1.39 (3H, t, J=8Hz), 3.22 and 3.52 (2H, ABq, J=18Hz), 4.03 (2H, t, J=5Hz), 4.37 [2H, t, J=5Hz), 4.42 (2H, q, J=8Hz), 5.27 (1H, d, J=5Hz), 5.38 (1H, br s), 5.91 (1H, d, J=5Hz), 6.57 (1H, d, J=3Hz), 7.57 (1H, d, J=2Hz), 8.01 (1H, d, J=2Hz), 8.11 (1H, d, J=3Hz).

PREPARATION 31

The following compounds were obtained according to a similar manner to that of Preparation 13.

(1) 1,7-Dimethyl-1H-imidazo[1,2-b]pyrazole

IR (Nujol): 3100, 1660, 1610, 1535 cm$^{-1}$. NMR DMSO-d$_6$, δ): 2.19 [3H, s), 3.68 (3H, s), 7.04 (1H, br s), 7.25 (1H, s), 7.40 (1H, br s).

(2) 1-Methyl-7-cyano-1H-imidazo-[1,2-b]pyrazole

IR (Nujol): 3100-3200, 2210, 1620 cm$^{-1}$. NMR (DMSO-d$_6$, δ): 3.78 (3H, s), 7.40 (1H, d, J=2Hz), 7.82 (1H, d, J=2Hz), 8.09 (1H, d, J=1Hz).

(3) 1-Methyl-7-methoxycarbonyl-1H-imidazo[1,2-b]pyrazole

IR (Nujol): 3150, 1690, 1600 cm$^{-1}$.
NMR (DMSO-d$_6$, δ): 3.74 (3H, s), 3.95 (3H, s), 7.31 (1H, d, J=2Hz), 7.74 (1H, d, J=2Hz), 7.93 (1H, s).

(4) 1,2-Dimethyl-1H-imidazo[1,2-b]pyrazole

IR {Neat): 1600 cm$^{-1}$.
NMR (DMSO-d$_6$, δ): 2.23 (3H, s), 3.49 (3H, s), 5.63 (1H, d, J=2Hz), 7.29 (1H, s), 7.38 (1H, d, J=2Hz)

PREPARATION 32

To a solution of 1-ethoxycarbonylmethyl-1H-imidazo-[1,2-b]pyrazole (35 g) in ethanol (180 ml) was added 28% ammonium hydroxide solution (110 ml). The mixture was stirred at room temperature for two hours. The resultant precipitate was collected by filtration, washed with isopropyl ether and dried to give 1-carbamoylmethyl-1H-imidazo[1,2-b]pyrazole (18.0 g).

NMR (DMSO-d$_6$, δ): 4.55 (2H, s), 5.63 (1H, d, J=2Hz), 7.11 (1H, d, J=3Hz), 7.28 (1H, br s), 7.45 (1H, d, J=3Hz), 7.51 (1H, d, J=2Hz), 7.58 (1H, br s).

PREPARATION 33

The following compound was obtained by treating 1-(1-methoxycarbonyl-1-methylethyl)-1H-imidazo[1,2-b]-pyrazole according to a similar manner to that of Preparation 32.

1-(1-Carbamoyl-1-methylethyl)-1H-imidazo[1,2-b]pyrazole

NMR (DMSO-d$_6$, δ): 1.68 (6H, s), 5.61 (1H, d, J=2Hz), 7.20 (1H, d, J=3Hz), 7.45 (1H, d, J=3Hz), 7.27 (2H, br s), 7.55 (1H, d, J=2Hz)

PREPARATION 34

To a suspension of lithium aluminum hydride (7.86 g) in tetrahydrofuran (500 ml) was added 1-carbamoylmethyl-1H-imidazo[1,2-b]pyrazole (17 g) at 50° C.

The mixture was refluxed for 3 hours. The reaction mixture was cooled at 5° C. Sodium fluoride (34.8 g) and water (11.2 ml) were added thereto under ice-cooling. The insoluble material was filtered off and the filtrate was evaporated to give 1-(2-aminoethyl)-1H-imidazo[1,2-b]-pyrazole.

PREPARATION 35

A mixture of acetic anhydride (19.5 ml) and formic acid (15.7 ml) was stirred at room temperature for 45 minutes. The mixture was cooled at 5° C. and 1-(2-aminoethyl)-1H-imidazo[1,2-b]pyrazole was added thereto. The mixture was stirred for 1 hour under ice-cooling. The reaction mixture w.._ evaporated and the residue was subjected to column chru... '~graphy on silica gel using a mixture of ethyl acetate and m.. 'r' (9:1) as eluent. Fractions containing the object compound were combined and evaporated to give 1-(2-formylaminoethyl)-1H-imidazo[1,2-b]pyrazole (7 g).

NMR (DMSO-d$_6$, δ): 3.36–3.50 (2H, m), 3.93–4.08 (2H, m), 5.73 (1H, d, J=3Hz), 7.16 (1H, d, J=2Hz), 7.37

(1H, d, J=2Hz), 7.47 (1H, d, J=3Hz), 8.15 (1H, s), 8.16 (1H, br s).

PREPARATION 36

The following compound was obtained according to a similar manner to that of Preparation 21.

1-(1-Methoxycarbonyl-1-methylethyl)-1H-imidazo-[1,2-b]pyrazole

NMR (DMSO-d$_6$, δ): 1.79 (6H, s), 3.64 (3H, s), 5.65 (1H, d, J=2Hz), 7.30 (1H, d, J=3Hz), 7.47 (1H, d, J=3Hz), 7.59 (1H, d, J=2Hz).

PREPARATION 37

To a solution of 1-ethoxycarbonylmethyl-1H-imidazo-[1,2-b]pyrazole (7.0 g) in ethanol (35 ml) was added 50% dimethylamine aqueous solution (17 ml). The mixture was stirred at room temperature for 5 hours. The reaction mixture was evaporated in vacuo. The resultant crude powder was subjected to column chromatography on silica gel using a mixture of ethyl acetate and methanol as an eluent. Fractions containing the object compound were combined and evaporated in vacuo. The resultant precipitate was collected and washed with diisopropyl ether to give 1-(N,N-dimethylcarbamoylmethyl)-1H-imidazo[1,2-b]-pyrazole (1.6 g).

IR (Nujol): 3100, 1660, 1600, 1500 cm$^{-1}$.

NMR (DMSO-d$_6$, δ): 2.84 (3H, s), 3.01 (3H, s), 4.90 (2H, s), 5.61 (1H, d, J=3Hz), 7.03 (1H, br s), 7.43 (1H, br s), 7.50 (1H, d, J=3Hz)

PREPARATION 38

To a solution of hydrazinoacetaldehyde diethyl acetal (52.6 g) in ethanol (110 ml) was added dropwise a solution of ethoxymethylenemalononitrile (41.5 g) in ethanol (420 ml) at room temperature. The mixture was stirred at ambient temperature for 24 hours. The reaction mixture was evaporated in vacuo. To the residue was added diethyl ether (400 ml) and the resultant precipitate was filtered off. The filtrate was subjected to column chromatography on silica gel using a mixture of ethyl acetate and hexane (2:3) as an eluent. Fractions containing the object compound were combined and evaporated to give 5-amino-4-cyano-1-(2,2-diethoxyethyl)pyrazole (23.0 g).

IR (Nujol): 3400, 3300, 3150, 2200, 1650, 1565, 1530 cm$^{-1}$.

NMR (DMSO-d$_6$, δ): 1.05 (6H, t, J=7Hz), 3.33–3.48 (2H, m), 3.55–3.70 (2H, m), 3.98 (2H, d, J=6Hz), 4.78 (1H, t, J=6Hz), 6.54 (2H, br s), 7.55 (1H, s)

PREPARATION 39

A solution of 5-amino-4-cyano-1-(2,2-diethoxyethyl)-pyrazole (23 g) in 1N hydrochloric acid (205 ml) was heated at 60–70° C. The mixture was stirred for 0.5 hour at the same condition. The reaction mixture was cooled under ice-water and the resultant solid was collected by filtration, washed with ice-water and dried over phosphorus pentoxide in vacuo to the crude product. The product was crystallized from ethanol (400 ml) to give 7-cyano-1H-imidazo[1,2-b]pyrazole (12.4 g).

IR (Nujol): 2210, 1620 cm$^{-1}$.

NMR (DMSO-d$_6$, δ): 7.42 (1H, dd, J=1Hz, 2Hz), 7.82 [1H, d, J=2Hz), 8.09 (1H, d, J=1Hz), 12.38 (1H, br s).

PREPARATION 40

7-Cyano-1H-imidazo[1,2-b]pyrazole (3 g) was added to conc. sulfuric acid under ice-cooling. The mixture was stirred at room temperature for 45 minutes. The reaction mixture was cooled at 0°–5° C. and carefully poured into ice water (30 ml). The aqueous solution was neutralized with conc. ammonium hydroxide solution and stirred for 1 hour under ice-cooling. The precipitate was collected, washed with cold water and dried over phosphorus pentoxide in vacuo to give 7-carbamoyl-1H-imidazo[1,2-b]pyrazole (3.45 g).

IR (Nujol): 3100–3500, 1690, 1650, 1620 cm$^{-1}$.

NMR (DMSO-d$_6$, δ): 7.05 (2H, br s), 7.20 (1H, dd, J=1Hz, 2Hz), 7.61 (1H, d, J=2Hz), 8.02 (1H, d, J=1Hz), 10.49 (1H, br s).

PREPARATION 41

The following compound was obtained according to a similar manner to that of Preparation 40.

1-Methyl-7-carbamoyl-1H-imidazo[1,2-b]pyrazole

IR (Nujol): 3350, 3150, 1680, 1620, 1600 cm$^{-1}$.

NMR (DMSO-d$_6$, δ): 4.00 (3H, s), 7.22 (1H, dd, J=1Hz, 2Hz), 7.63 (1H, d, J=2Hz), 8.05 (1H, d, J=1Hz)

PREPARATION 42

A solution of 5-amino-4-carboxy-1-(2,2-diethoxyethyl)pyrazole (50 g) in 80% trifluoroacetic acid aqueous solution (250 ml) was stirred at room temperature for two days. The reaction mixture was evaporated in vacuo. The resultant solid was washed with cold water, collected by filtration and dried over phosphorus pentoxide in vacuo to give 7-carboxy-1H-imidazo[1,2-b]-pyrazole (17.10 g).

NMR (DMSO-d$_6$, δ): 7.27 (1H, s), 7.70 (1H, s), 7.89 (1H, s), 12.04 (1H, br s).

PREPARATION 43

To a solution of 5-amino-1-(2,2-diethoxyethyl-4-carboxypyrazole (50 g) in N,N-dimethylformamide (150 ml) was added potassium carbonate (28.4 g) under ice-cooling. After stirring at 5° C. for 30 minutes, to the mixture was added methyl iodide (25.6 ml). The mixture was stirred at the same condition for 3 hours. The reaction mixture was poured into a mixture of ethyl acetate (1 l) and water (1 l). The separated organic layer was washed with water and brine and dried over magnesium sulfate. The solvent was evaporated in vacuo to give 5-amino-1-(2,2-diethoxyethyl)-4-methoxycarbonyl-pyrazole (43.02 g).

IR (Nujol): 2900–3000, 1680, 1630 cm$^{-1}$.

NMR (DMSO-d$_6$, δ): 1.05 (6H, t, J=7Hz), 3.33–3.70 (4H, m), 4.00 (2H, d, J=6Hz), 4.79 (1H, t, J=6Hz), 6.25 (2H, br s), 7.48 (1H, s).

PREPARATION 44

The following compound was obtained according to a similar manner to that of Preparation '.

7-Methoxycarbonyl-1H-imidazo[1,2-b]pyrazole

IR (Nujol) 1680, 1620, 1550 cm$^{-1}$.

NMR (DMSO-d$_6$, δ): 3.76 (3H, s), 7.32 (1H, dd, J=1Hz, 2Hz), 7.74 (1H, d, J=2Hz), 7.95 (1H, s), 12.12 (1H, br s).

PREPARATION 45

A solution of 1-methyl-7-methoxycarbonyl-1H-imidazo[1,2-b]pyrazole (5.0 g) in 4N-sodium hydroxide aqueous solution (14 ml) was refluxed for 1 hour. The reaction mixture was cooled with ice-bath and adjusted to pH 3.0 with 6N hydrochloric acid. The resultant solid was collected by filtration, washed with cold water and dried over phosphorus pentoxide in vacuo to give 7-carboxy-1-methyl-1H-imidazo[1,2-b]pyrazole (4.42 g).

IR (Nujol): 1660, 1600 cm$^{-1}$.

NMR (DMSO-d$_6$, δ): 3.97 (3H, s), 7.29 (1H, d, J=2Hz), 7.72 (1H, d, J=2Hz), 7.89 (1H, s).

PREPARATION 46

To a solution of 7-amino-1H-imidazo[1,2-b]pyrazole dihydrochloride (10 g) in pyridine (100 ml) was added dropwise acetyl chloride (7.3 ml) under ice-cooling. The mixture was stirred at room temperature for two hours. The reaction mixture was poured into ice water (200 ml) and extracted with a mixture of ethyl acetate (200 ml) and tetrahydrofuran (300 ml). The organic layer was dried over magnesium sulfate and the solvent was evaporated to give 1-acetyl-7-acetylamino-1H-imidazo[1,2-b]pyrazole (3.13 g).

IR (Nujol): 3350, 1680, 1660 cm$^{-1}$.

NMR (DMSO-d$_6$, δ): 2.01 (3H, s), 2.53 (3H, s), 7.70 (1H, d, J=2Hz), 7.82 (1H, d, J=2Hz), 7.88 (1H, s), 9.15 (1H, br s).

PREPARATION 47

Triphenylmethyl chloride (154.98 g) was added to a solution of triethylamine (154.97 ml) and 1-methoxycarbonylmethyl-5-aminopyrazole (71.88 g) in tetrahydrofuran (215.64 ml) and the mixture was stirred for three hours at ambient temperature. The reaction mixture was added to a mixture of water (300 ml) and ethyl acetate (200 ml). The organic layer was separated and dried over magnesium sulfate. The magnesium sulfate was filtered off, and the filtrate was evaporated under reduced pressure to give 1-methoxycarbonylmethyl-5-triphenylmethylaminopyrazole.

IR (Nujol) 1720, 1550, 750, 700 cm$^{-1}$.

NMR (DMSO-d$_6$, δ): 3.72 (3H, s), 4.52 (1H, d, J=1.9Hz), 4.97 (2H, s), 6.54 (1H, s), 6.87 (1H, d, J=1.9Hz), 7.18-7.33 (15H, m).

PREPARATION 48

4N Sodium hydroxide aqueous solution (125.79 ml) was added to a solution of 1-methoxycarbonylmethyl-5-triphenylmethylaminopyrazole (100 g) in dioxane (100 ml) and the mixture was stirred for three hours at ambient temperature. The reaction mixture was added to a mixture of ethyl acetate (300 ml) and tetrahydrofuran (300 ml), and 1N hydrochloric acid was added thereto to adjust to pH 3. The organic layer was separated and dried over magnesium sulfate. The magnesium sulfate was filtered off, and the filtrate was evaporated under reduced pressure to give 1-carboxymethyl-5-triphenylmethylamino-pyrazole.

IR (Nujol): 1700, 1230, 755, 740, 690 cm$^{-1}$.

NMR (DMSO-d$_6$, δ): 4.51 (1H, d, J=1.9Hz), 4.85 (2H, s), 6.49 (1H, s), 6.84 (1H, d, J=1.9Hz), 7.15-7.41 (15H, m).

PREPARATION 49

A solution of methyllithium in diethyl ether (250 ml) was added to a solution of 1-carboxymethyl-5-triphenylmethylaminopyrazole (25.95 g) in tetrahydrofuran (400 ml) under ice-cooling and the mixture was stirred for 6 hours at ambient temperature. The reaction mixture was added to a mixture of ice-cold water (500 ml) and diethyl ether (500 ml). The organic layer was separated and dried over magnesium sulfate. The magnesium sulfate was filtered off, and the filtrate was evaporated under reduced pressure to give 1-acetylmethyl-5-triphenylmethylaminopyrazole.

IR (Nujol): 1720, 1540, 750, 700 cm$^{-1}$.

NMR (DMSO-d$_6$, δ): 2.01 (3H, s), 4.58 (1H, d, J=1.9Hz), 4.92 (2H, s), 6.47 (1H, s), 6.90 (1H, d, J=1.9Hz), 7.18-7.31 (15H, m).

PREPARATION 50

The following compound was obtained according to a similar manner to that of Preparation 3.

1-Formyl-2-methyl-1H-imidazo[1,2-b]pyrazole

IR (Nujol): 1680, 1550, 930, 740 cm$^{-1}$.

NMR (DMSO-d$_6$, δ): 2.46 (3H, s), 6.21 (1H, d, J=1.9Hz), 7.61 (1H, s), 7.61 (1H, d, J=1.9Hz), 9.03 (1H, s).

PREPARATION 51

To a solution of 1H-imidazo[1,2-b]pyrazole (2 g) in tetrahydrofuran (20 ml) were added N,N-dimethylcarbamoyl chloride (3.8 ml) and triethylamine (6.2 ml) at 20° C. under stirring. After stirring, the reaction mixture was poured into a mixture of ethyl acetate (30 ml) and cold water (50 ml). The ethyl acetate layer was separated, washed with water and a saturated aqueous solution of sodium chloride, dried over magnesium sulfate and evaporated in vacuo to give 1-(N,N-dimethylcarbamoyl)-1H-imidazo[1,2-b]pyrazole (3.0 g).

NMR (DMSO-d$_6$, δ): 3.00 (6H, s), 5.94 (1H, d, J=3Hz), 7.49 (1H, d, J=2Hz), 7.62 (1H, d, J=2Hz), 7.79 (1H, d, J=3Hz).

PREPARATION 52

To a solution of 1H-imidazo[1,2-b]pyrazole (2.5 g) in tetrahydrofuran (10 ml) was added acetic anhydride (3.1 ml) under stirring at 35° C. and the mixture was stirred for 2 hours at the same temperature. The reaction mixture was evaporated in vacuo to give 1-acetyl-1H-imidazo[1,2-b]-pyrazole (2.7 g).

IR (Nujol): 1710, 1585, 1540 cm$^{-1}$.

NMR (DMSO-d$_6$, δ): 2.55 (3H, s), 6.19 [1H, d, J=3Hz), 7.66 (1H, d, J=2Hz), 7.10 (1H, br s), 7.78 (1H, d, J=3Hz).

PREPARATION 53

The following compounds were obtained according to a similar manner to that of Preparation 5.

(1) Benzhydryl 7β-(t-butoxycarbonylamino)-3-[1-·' ᵗʰyl-5-(1H-imidazo[1,2-b]pyrazolio)]methyl-3-cephem-ᴛ-ᴋ ˙ ᵗ˜ʳʸ, late iodide NMR (DMSO-d$_6$, δ): 1.41 (9H, s), 2.71 [3H, s), 3.30-3.50 (2H, m), 5.15 (1H, d, J=5Hz), 5.44 and 5.55 (2H, ABq, J=18Hz), 5.50-5.70 (1H, m), 6.92 (1H, s), 6.97 (1H, d, J=3Hz), 7.22-7.53 (10H, m), 8.07 (1H, d, J=10Hz), 8.22 (1H, d, J=2Hz), 8.28 (1H, m), 8.40 (1H, d, J=3Hz).

(2) Benzhydryl 7β-(t-butoxycarbonylamino)-3-[1-(N,N-dimethylcarbamoyl)-5-(1H-imidazo[1,2-b]pyrazolio)]methyl-3-cephem-4-carboxylate iodide NMR (DMSO-d$_6$, δ): 1.35–1.51 (9H, m), 3.10 (6H, s), 3.20–3.68 (2H, m), 5.16 (1H, d, J=5Hz), 5.39 and 5.48 (2H, ABq, J=14Hz), 5.66 (1H, dd, J=5Hz, 8Hz), 6.77 (1H, d, J=3Hz), 6.95 (1H, s), 7.08–7.60 (10H, m), 8.08 (1H, d, J=2Hz), 8.15 (1H, d, J=2Hz), 8.33 (1H, d, J=3Hz).

(3) Benzhydryl 7β-(t-butoxycarbonylamino)-3-[1,2-dimethyl-5-(1H-imidazo[1,2-b]pyrazolio)]methyl-3-cephem-4-carboxylate iodide IR (Nujol): 1780, 1710, 1600 cm$^{-1}$.
NMR (DMSO-d$_6$, δ): 1.40 (9H, s), 2.30 (3H, s), 3.37 (2H, br s), 3.70 (3H, s), 5.12 (1H, d, J=5Hz), 5.20 and 5.40 (12H, ABq, J=15Hz), 5.56 (1H, dd, J=8Hz, 5Hz), 6.63 (1H, d, J=3Hz), 6.90 (1H, s), 7.10–7.50 (10H, m), 7.57 (1H, s), 8.01 (1H, d, J=3Hz).

(4) Benzhydryl 7β-(t-butoxycarbonylamino)-3-[1-acetyl-7-acetylamino-5-(1H-imidazo[1,2-b]pyrazolio)]methyl-3-cephem-4-carboxylate iodide NMR (DMSO-d$_6$, δ): 1.41 (9H, s), 2.10 (3H, s), 2.53 (3H, s), 3.42 (2H, br s), 5.15 (1H, d, J=5Hz), 5.13–5.30 (2H, m), 5.63 (1H, dd, J=5Hz, 8Hz), 6.94 (1H, s), 7.29–7.54 (10H, m), 7.60 (1H, br s), 7.70 (1H, d, J=2Hz), 8.04 (1H, s), 8.10 (1H, d, J=8Hz)

(5) Benzhydryl 7β-(t-butoxycarbonylamino)-3-[7-carboxy-1-methyl-5-(1H-imidazo[1,2-b]pyrazolio)]methyl-3-cephem-4-carboxylate iodide NMR (DMSO-d$_6$, δ): 1.41 (9H, s), 3.60 (2H, br s), 4.01 (3H, s), 5.15 (1H, d, J=5Hz), 5.30 and 5.50 (2H, ABq, J=15Hz), 5.63 (1H, dd, J=5Hz, 8Hz), 6.73 (1H, s), 7.20–7.45 (10H, m), 7.80 (1H, br s), 7.86 (1H, br s), 8.02 (1H, d, J=8Hz), 8.63 (1H, s).

(6) Benzhydryl 7β-(t-butoxycarbonylamino)-3-[1-methyl-7-methoxycarbonyl-5-(1H-imidazo[1,2-b]pyrazolio)]methyl-3-cephem-4-carboxylate iodide NMR (DMSO-d$_6$, δ): 1.41 (9H, s), 3.48 (2H, br s), 3.94 (3H, s), 4.22 (3H, s), 5.15 (1H, d, J=5Hz), 5.34 and 5.55 (2H, ABq, J=16Hz), 5.65 (1H, dd, J=5Hz, 8Hz), 6.92 (1H, s), 7.27–7.50 (10H, m), 7.83 (1H, br s), 7.91 (1H, d, J=2Hz), 8.08 (1H, d, J=8Hz), 8.74 (1H, s).

(7) Benzhydryl 7β-(t-butoxycarbonylamino)-3-[1-methyl-7-carbamoyl-5-(1H-imidazo[1,2-b]pyrazolio)]methyl-3-cephem-4-carboxylate iodide IR (Nujol): 1780, 1000, 1650 cm$^{-1}$.
NMR (DMSO-d$_6$, δ): 1.41 (9H, s), 3.48 (2H, br s), 4.09 (3H, s), 5.14 (1H, d, J=5Hz), 5.34 and 5.48 (2H, ABq, J=16Hz), 5.66 (1H, dd, J=5, 8Hz), 6.94 (1H, s), 7.22–7.60 (10H, m), 7.62 (1H, br s), 7.95 (1H, br s), 8.06 (1H, d, J=8Hz), 8.64 (1H, s)

(8) Benzhydryl 7β-(t-butoxycarbonylamino)-3-[7-carbamoyl-5-(1H-imidazo[1,2-b]pyrazolio)]methyl-3-cephem-4-carboxylate iodide NMR (DMSO-d$_6$, δ): 1.41 (9H, s), 3.51 (2H, br s), 5.16 (1H, d, J=5Hz), 5.34 and 5.48 (2H, ABq, J=15Hz), 5.66 (1H, dd, J5, 8Hz), 7.05 (1H, s), 7.26–7.50 (10H, m), 7.60 (1H, br s), 7.95 (1H, br s), 8.02 (1H, d, J=8Hz), 8.64 (1H, s).

(9) Benzhydryl 7β-(t-butoxycarbonylamino)-3-[1-(N,N-dimethylcarbamoylmethyl)-5-(1H-imidazo[1,2-b]pyrazolio)]-methyl-3-cephem-4-carboxylate iodide IR (Nujol): 1780, 1710, 1650 cm$^{-1}$.
NMR (DMSO-d$_6$, δ): 1.41 (9H, s), 2.88 (3H, s), 3.06 (3H, s), 3.44 (2H, br s), 5.19 (1H, d, J=5Hz), 5.29 (2H, s), 5.28 and 5.46 (2H, ABq, J=15Hz), 5.65 (1H, dd, J=5, 8Hz), 6.63 (1H, d, J=3Hz), 6.97 (1H, s), 7.26–7.64 (10H, m), 7.64 (1H, d, J=2Hz), 7.86 (1H, d, J=2Hz), 8.07 (1H, d, J=8Hz), 8.14 (1H, d, J=3Hz).

(10) Benzhydryl 7β-(t-butoxycarbonylamino)-3-[1-(1-carbamoyl-1-methylethyl)-5-(1H-imidazo[1,2-b]pyrazolio)]-methyl-3-cephem-4-carboxylate iodide NMR (DMSO-d$_6$, δ): 1.40 (9H, s), 1.84 (6H, s), 3.37 (2H, br s), 5.17 (1H, d, J=5Hz), 5.29 and 5.43 (2H, ABq, J=15Hz), 5.62 (1H, dd, J=5Hz, 8Hz), 6.68 (1H, d, J=3Hz), 6.94 (1H, s), 7.20–7.60 (10H, m), 7.85 (1H, br s), 7.99 (1H, br s), 8.07 (1H, d, J=8Hz), 8.13 (1H, d, J=3Hz).

(11) Benzhydryl 7β-(t-butoxycarbonylamino)-3-[1-(2-formylaminoethyl)-5-(1H-imidazo[1,2-b]pyrazolio)]methyl-3-cephem-4-carboxylate iodide IR (Nujol): 1780, 1710, 1570 cm$^{-1}$.
NMR (DMSO-d$_6$, δ): 1.40 (9H, s), 3.37 (2H, br s), 3.51–3.63 (2H, m), 4.23 (2H, t, J=6Hz), 5.13 (1H, d, J=5Hz), 5.33 and 5.49 (2H, ABq, J=16Hz), 5.64 (1H, dd, J=5, 8Hz), 6.73 (1H, d, J=3Hz), 6.96 (1H, s), 7.18–7.53 (10H, m), 7.76 (1H, br s), 7.80 (1H, br s), 7.94 (1H, s), 8.08 (1H, d, J=8Hz), 8.18 (1H, d, J=3Hz)

(12) Benzhydryl 7β-(t-butoxycarbonylamino)-3-[1-carbamoylmethyl-5-(1H-imidazo[1,2-b]pyrazolio)]methyl-3-cephem-4-carboxylate iodide

(13) Benzhydryl 7β-(t-butoxycarbonylamino)-3-[1,7-dimethyl-5-(1H-imidazo[1,2-b]pyrazolio)]methyl-3-cephem-4-carboxylate iodide IR (Nujol): 1775, 1710, 1655, 1605 cm$^{-1}$.
NMR (DMSO-d$_6$, δ): 1.42 (9H, s), 2.26 (3H, s), 3.41 (2H, s), 3.89 (3H, s), 5.09 and 5.25 (2H, ABq, J=16Hz), 5.16 (1H, d, J=5Hz), 5.58 (1H, dd, J=' 8Hz, 5Hz), 6.92 (1H, s), 7.05–7.46 (10H, m), 7.62 (1H, m), 7.12 (1H, m), 7.83 (1H, m), 7.95 (1H, d, J=8Hz)

PREPARATION 54

The following compounds were obtained according to a similar manner to that of Preparation 27.

(1)

7β-Amino-3-[1,7-dimethyl-5-(1H-imidazo[1,2-b]-pyrazolio)]methyl-3-cephem-4-carboxylate bis(trifluoroacetate)

IR (Nujol): 1785, 1670 cm$^{-1}$.

NMR (D$_2$O, δ): 2.36 (3H, s), 3.26 and 3.51 (2H, ABq, J=18Hz), 3.93 (3H, s), 5.16 (1H, d, J=5Hz), 5.27 (1H, d, J=5Hz), 5.30 (2H, s), 7.35 (1H, m), 7.75 (2H, m).

(2)

7β-Amino-3-[1-(1-carbamoyl-1-methylethyl)-5-(1H-imidazo[1,2-b]pyrazolio)]methyl-3-cephem-4-carboxylate bis(trifluoroacetate)

NMR (DMSO-d$_6$, δ): 1.85 (6H, s), 3.39 and 3.59 (2H, ABq, J=18Hz), 5.26 (2H, s), 5.48 (2H, s), 6.72 (1H, d, J=3Hz), 7.54 (1H, br s), 7.58 (1H, br s), 7.92 (1H, d, J=2Hz), 8.20 (1H, d, J=2Hz), 8.28 (1H, d, J=3Hz)

(3)

7β-Amino-3-[1-methyl-7-methoxycarbonyl-5-(1H-imidazo-[1,2-b]pyrazolio)]methyl-3-cephem-4-carboxylate bis(trifluoroacetate)

NMR (DMSO-d$_6$, δ): 3.45 and 3.58 (2H, ABq, J=18Hz), 3.89 (3H, s), 4.08 (3H, s), 5.23 and 5.28 (2H, ABq, J=5Hz), 5.54 (2H, br s), 7.88 (1H, d, J=2Hz), 8.22 (1H, d, J=2Hz), 8.91 (1H, s).

(4)

7β-Amino-3-[7-carboxy-1-methyl-5-(1H-imidazo[1,2-b]-pyrazolio)]methyl-3-cephem-4-carboxylate bis(trifluoroacetate)

NMR (DMSO-d$_6$, δ): 3.47 and 3.60 (2H, ABq, J=18Hz), 4.09 (3H, s), 5.21–5.30 (2H, m), 5.52 (2H, br s), 7.86 (1H, br s), 8.19 (1H, br s), 8.78 (1H, s).

(5)

7β-Amino-3-[1-acetyl-7-acetylamino-5-(1H-imidazo-[1,2-b]pyrazolio)]methyl-3-cephem-4-carboxylate bis(trifluoroacetate)

NMR (DMSO-d$_6$, δ): 2.00 (3H, s), 2.11 (3H, s), 3.39 and 3.53 (2H, ABq, J=18Hz), 5.10 (1H, d, J=5Hz), 5.23 (2H, br s), 5.61 (1H, dd, J=5Hz, 8Hz), 7.70 (1H, br s), 8.06 (1H, d, J=2Hz), 8.23 (1H, d, J=8Hz), 8.68 (1H, s).

(6)

7β-Amino-3-[2-methyl-5-(1H-imidazo[1,2-b]pyrazolio)]-methyl-3-cephem-4-carboxylate tris(trifluoroacetate)

IR (Nujol): 1780, 1200, 720 cm$^{-1}$.

NMR (DMSO-d$_6$, δ): 2.40 (3H, s), 3.50 (2H, br s), 5.05 (1H, m), 5.20 (2H, s), 5.50 (1H, m), 5.53 (1H, d, J=3Hz), 7.76 (1H, s), 8.15 (1H, d, J=3Hz).

(7)

7β-Amino-3-[1,2-dimethyl-5-(1H-imidazo[1,2-b]-pyrazolio)]methyl-3-cephem-4-carboxylate tris(trifluoroacetate)

IR (Nujol): 1780, 1660, 1600 cm$^{-1}$.

NMR (DMSO-d$_6$+D$_2$O, δ): 2.36 (3H, s), 3.40 (2H, m), 3.70 (3H, s), 5.16 (2H, m), 5.36 (2H, s), 6.62 (1H, d, J=3Hz), 7.76 (1H, s), 8.06 (1H, d, J=3Hz).

(8)

7β-Amino-3-[1-(N,N-dimethylcarbamoyl)-5-(1H-imidazo-[1,2-b]pyrazolio)]methyl-3-cephem-4-carboxylate bis(trifluoroacetate)

NMR (DMSO-d$_6$, δ): 3.10 (6H, s), 3.40–3.60 (2H, m), 5.21–5.33 (2H, m), 5.38–5.61 (2H, m), 6.81 (1H, d, J=3Hz), 8.13 (1H, d, J=2Hz), 8.31 (1H, d, J=2Hz), 8.45 (1H, d, J=2Hz)

PREPARATION 55

A solution of benzhydryl 7β-(t-butoxycarbonylamino)-3-[1-carbamoylmethyl-5-(1H-imidazo[1,2-b]pyrazolio)]-methyl-3-cephem-4-carboxylate iodide (4.7 g) in a mixture of formic acid (18.8 ml) and conc. hydrochloric acid (1.0 ml) was stirred at room temperature for 2 hours. The reaction mixture was poured into a mixture of acetone (140 ml) and ethyl acetate (280 ml). The resultant precipitate was collected by filtration, washed with diisopropyl ether and dried over phosphorus pentoxide in vacuo to give 7β-amino-3-[1-carbamoylmethyl-5-[1H-imidazo[1,2-b]-pyrazolio)]methyl-3-cephem-4-carboxylic dihydrochloride (2.73 g).

NMR (DMSO-d$_6$, δ): 3.42, 3.58 (2H, ABq, J=18Hz), 4.97 (2H, s), 5.25 (2H, s), 5.54 (2H, s), 6.73 (1H, d, J=3Hz), 7.49 (1H, s), 7.81 (1H, d, J=2Hz), 7.96 (1H, s), 8.16 (1H, d, J=2Hz), 8.36 (1H, d, J=3Hz)

PREPARATION 56

The following compounds were obtained according to a similar manner to that of Preparation 55.

(1)

7β-Amino-3-[1-(2-formylaminoethyl)-5-(1H-imidazopyrazolio)]methyl-3-cephem-4-carboxylate dihydrochloride IR (Nujol): 1780, 1730, 1710, 1670, 1600 cm$^{-1}$.

NMR (DMSO-d$_6$, δ): 3.37 and 3.49 (2H, ABq, J=18Hz), 3.34 (2H, t, J=6Hz), 4.29 (2H, t, J=6Hz), 5.23 (2H, s), 5.53 (2H, s), 6.80 (1H, d, J=3Hz), 7.85 (1H, br s), 7.94 (1H, s), 8.11 (1H, d, J=br s), 8.34 (1H, d, J=3Hz), 8.39 (1H, br s).

(2)

7β-Amino-3-[1-(N,N-dimethylcarbamoylmethyl)-5-(1H-imidazo[1,2-b]pyrazolio)]methyl-3-cephem-4-carboxylate dihydrochloride NMR (DMSO-d$_6$, δ): 2.88 (3H, s), 3.06 (3H, s), 3.42 and 3.58 (2H, ABq, J=18Hz), 5.23 and 5.27 (2H, ABq, J=5Hz), 5.35 (2H, s), 5.55 (2H, s), 6.70 (1H, d, J=3Hz), 7.74 (1H, br s), 8.18 (1H, br s), 8.36 (1H, d, J=3Hz).

(3)

7β-Amino-3-[7-carbamoyl-5-(1H-imidazo[1,2-b]-pyrazolio)]methyl-3-cephem-4-carboxylate dihydrochloride NMR (DMSO-d$_6$, δ): 3.56 and 3.71 (2H, ABq, J=18Hz), 5.28 (2H, br s), 5.54 (2H, s), 7.81 (1H, br s), 8.23 (1H, br s), 8.94 (1H, s)

(4)

7β-Amino-3-[1-methyl-7-carbamoyl-5-(1H-imidazo[1,2-b]pyrazolio)]methyl-3-cephem-4-carboxylate dihydrochloride IR (Nujol): 1780, 1700, 1660, 1600 cm$^{-1}$.

NMR (DMSO-d$_6$, δ): 3.56 and 3.73 (2H, ABq, J=18Hz), 4.12 (3H, s), 5.26 and 5.31 (2H, ABq, J=5Hz), 5.54 (2H, s), 7.86 (1H, br s), 8.28 (1H, br s), 9.07 (1H, s).

(5)
7β-Amino-3-[1-acetyl-5-(1H-imidazo[1,2-b]pyrazolio)]-methyl-3-cephem-4-carboxylate dihydrochloride NMR (D₂O, δ): 2.80 (3H, s), 3.30–3.81 (2H, m), 5.10–5.70 (4H, m), 6.95 (1H, d, J=3Hz), 7.95–8.25 (2H, m), 8.35 (1H, d, J=3Hz).

PREPARATION 57

To a suspension of 7β-amino-3-[1-acetyl-5-(1H-imidazo[1,2-b]pyrazolio)]methyl-3-cephem-4-carboxylate dihydrochloride (1 g) in methanol (10 ml) was added hydrochloric acid (0.65 ml) under stirring at 25° C. The mixture was stirred for 3 hours at 30° C. The reaction mixture was poured into ethyl acetate (400 ml). The resultant precipitates were collected by filtration to give 7β-amino-3-[5-(1H-imidazo[1,2-b]pyrazolio)]methyl-3-cephem-4-carboxylate trihydrochloride IR (Nujol): 1780, 1705, 1600, 1510 cm⁻¹.

NMR (D₂O, δ): 3.25–3.60 (2H, m), 5.10–5.38 (2H, m), 5.40–5.70 (2H, m), 6.48 (1H, d, J=3Hz), 7.58 [1H, d, J=2Hz), 7.85 (1H, d, J=2Hz), 8.03 (1H, J=3Hz).

PREPARATION 58

To a solution of 1-(2-oxopropyl)-5-triphenylmethyl-aminopyrazole (0.75 g) in methanol was added conc. hydrochloric acid (0.75 ml). The mixture was stirred for 2 hours. The reaction mixture was added to a mixture of ethyl acetate, tetrahydrofuran and ice-cold water, and the mixture was adjusted to pH 8 with sodium bicarbonate. The organic layer was separated and dried over magnesium sulfate. The magnesium sulfate was filtered off, and the filtrate was evaporated under reduced pressure The residue was pulverized with diisopropyl ether to give 2-methyl-1H-imidazo[1,2-b]pyrazole.

PREPARATION 59

Benzhydryl 7β-(t-butoxycarbonylamino)-3-chloromethyl-3-cephem-4-carboxylate (3.91 g) was added to N,N-dimethylformamide (4 ml) under stirring. Sodium iodide (1.14 g) and 1-formyl-2-methyl-1H-imidazo[1,2-b]-pyrazole (1.7 g) were added to the mixture. The mixture was stirred for 12 hours at ambient temperature. The reaction mixture was added to a mixture of ethyl acetate (230 ml) and ice-cold water (115 ml). The organic layer was separated, washed with brine and dried over magnesium sulfate. The magnesium sulfate was filtered off, and the filtrate was evaporated under reduced pressure. The residue was pulverized with diisopropyl ether to give benzhydryl 7β-(t-butoxycarbonylamino)-3-[2-methyl-5-(1H-imidazo[1,2-b]pyrazolio)]methyl-3-cephem-4-carboxylate iodide.

IR (Nujol): 1780, 1710, 1160 cm⁻¹.

NMR (DMSO-d₆, δ): 1.45 (9H, s), 2.33 [3H, s), 3.35 (2H, br s), 5.14 (1H, d, J=5Hz), 5.30 (2H, m), 5.60 (1H, dd, J=8Hz, 5Hz), 6.50 (1H, d, J=3Hz), 6.92 (1H, s), 7.1–7.6 (10H, m), 7.90 (1H, s), 7.95 (1H, d, J=8Hz), 8.01 (1H, d, J=3Hz)

EXAMPLE 7

The following compounds were obtained according to similar manners to those of Example 1, 2 and 5.

(1)
7β-[2-(2-Aminothiazol-4-yl)-2-methoxyiminoacetamido]-3-[1,7-dimethyl-5-(1H-imidazo[1,2-b]pyrazolio)]methyl-3-cephem-4-carboxylate (syn isomer)

IR (Nujol): 3280, 3100, 1760, 1660, 1605cm⁻¹.

NMR (DMSO-d₆, δ): 2.33 (3H, s), 2.90 and 3.35 (2H, ABq, J=17Hz), 3.80 (3H, s), 3.89 (3H, s), 4.98 (1H, d, J=5Hz), 5.14 and 5.45 (2H, ABq, J=15Hz), 5.58 (1H, dd, J=8Hz, 5Hz), 6.66 (1H, s), 7.15 (2H, br s), 7.61 (1H, m), 8.08 (1H, m), 8.85 (1H, d, J=3Hz), 9.45 (1H, d, J=8Hz)

(2)
7β-[2-(5-Amino-1,2,4-thiadiazol-3-yl)-2-methoxyiminoacetamido]-3-[1,7-dimethyl-5-(1H-imidazo-[1,2-b]pyrazolio)]methyl-3-cephem-4-carboxylate (syn isomer)

IR (Nujol): 1775, 1675, 1630, 1605cm⁻¹.

NMR (DMSO-d₆, δ): 2.31 (3H, s), 2.78 and 3.31 (2H, ABq, J=18Hz), 3.88 (6H, s), 4.96 (1H, d, J=5Hz), 5.13 and 5.44 (2H, ABq, J=16Hz), 5.59 (1H, dd, J=8Hz, 5Hz), 7.61 (1H, m), 8.08 (3H, m), 8.85 (1H, d, J=3Hz), 9.41 (1H, d, J=8Hz)

(3)
7β-[2-(5-Amino-1,2,4-thiadiazol-3-yl)-2-ethoxyiminoacetamido]-3-[6-methyl-5-(1H-imidazo[1,2-b]-pyrazolio)]methyl-3-cephem-4-carboxylate (syn isomer)

IR (Nujol): 1760, 1670, 1600 cm⁻¹.

NMR (D₂O, δ): 1.31 (3H, t, J=7Hz), 2.51 (3H, s), 3.13 and 3.33 (2H, ABq, J=18Hz), 4.32 (2H, q, J=7Hz), 5.16 (1H, d, J=5Hz), 5.21 (2H, br s), 5.82 (1H, d, J=5Hz), 6.17 (1H, s), 7.32 (1H, br s), 7.80 (1H, br s).

(4)
7β-[2-(2-Aminothiazol-4-yl)-2-methoxyiminoacetamido]-3-[1-carbamoylmethyl-5-(1H-imidazo[1,2-b]pyrazolio)]-methyl-3-cephem-4-carboxylate (syn isomer)

IR Nujol): 1770, 1680, 1600 cm⁻¹.

NMR (DMSO-d₆, δ): 3.30 (2H, br s), 3.80 (3H, s), 4.90 (2H, s), 5.02 (1H, d, J=5Hz), 5.22 and 5.55 (2H, ABq, J=15Hz), 5.60 (1H, dd, J=5Hz, 8Hz), 6.55 (1H, d, J=3Hz), 6.67 (1H, s), 7.13 (2H, br s), 7.37 (1H, br s), 7.65 (1H, br s), 7.83 (1H, br s), 8.31 (1H, d, J=3Hz), 8.98 (1H, br s), 9.46 (1H, d, J=8Hz)

(5)
7β-[2-(5-Amino-1,2,4-thiadiazol-3-yl)-2-methoxyiminoacetamido]-3-[1-carbamoylmethyl-5-(1H-imidazo-[1,2-b]pyrazolio)]methyl-3-cephem-4-carboxylate (syn isomer)

IR (Nujol): 3300, 3100, 1775. 1680, 1600 cm⁻¹.

NMR (DMSO-d₆, δ): 2.80 and 3.41 (2H, ABq, J=18Hz), 3.85 (3H, s), 4.90 (2H, br s), 4.97 (1H, d, J=5Hz), 5.22 and 5.58 (2H, ABq, J=13Hz), 5.62 (1H, dd, J=5Hz, 8Hz), 6.55 (1H, d, J=3Hz), 7.37 (1H, br s), 7.64 (1H, d, J=2Hz), 7.89 (1H, br s), 8.10 (2H, br s), 8.32 (1H, d, J=3Hz), 8.97 (1H, d, J=2Hz), 9.45 (1H, d, J=8Hz).

(6)

7β-[2-(5-Amino-1,2,4-thiadiazol-3-yl)-2-ethoxyiminoacetamido]-3-[1-carbamoylmethyl-5-(1H-imidazo[1,2-b]pyrazolio)]methyl-3-cephem-4-carboxylate (syn isomer)

IR (Nujol): 1765, 1680, 1600, 1520 cm$^{-1}$.

NMR (DMSO-d$_6$, δ): 1.20 (3H, t, J=7Hz), 2.80 and 3.34 (2H, ABq, J=17Hz), 4.12 (2H, q, J=7Hz), 4.89 (2H, s), 5.02 (1H, d, J=5Hz), 5.23 and 5.54 (2H, ABq, J=15Hz), 5.64 (1H, dd, J=5Hz, 8Hz), 6.59 (1H, d, J=3Hz), 7.47 [1H, s], 7.69 (1H, br s), 7.86 [1H, s], 8.16 (2H, s), 8.35 (1H, d, J=3Hz), 9.07 (1H, d, J=2Hz), 9.52 (1H, d, J=8Hz).

(7)

7β-[2-(5-Amino-1,2,4-thiadiazol-3-yl)-2-methoxyiminoacetamido]-3-[1-(2-formylaminoethyl)-5-(1H-imidazo[1,2-b]pyrazolio)]methyl-3-cephem-4-carboxylate (syn isomer)

IR (Nujol): 3350, 1770, 1660, 1600 cm$^{-1}$.

NMR (DMSO-d$_6$, δ): 2.80 and 3.32 (2H, ABq, J=18Hz), 3.40-3.67 (2H, m), 3.87 (3H, s), 4.10-4.40 (2H, m), 4.97 (1H, d, J=5Hz), 5.25 and 5.49 (2H, ABq, J=13Hz), 5.62 (1H, dd, J=5Hz, 8Hz), 6.62 (1H, d, J=3Hz), 7.72 (1H, br s), 7.92 (1H, br s), 8.09 (2H, br s), 8.32 (1H, d, J=3Hz), 8.85 (1H, br s), 9.44 (1H, d, J=8Hz)

(8)

7β-[2-(5-Amino-1,2,4-thiadiazol-3-yl)-2-methoxyiminoacetamido]-3-[1-(1-carbamoyl-1-methylethyl))-5-(1H-imidazo-[1,2-b]pyrazolio)]methyl-3-cephem-4-carboxylate (syn isomer)

IR (Nujol): 1760, 1680, 1610 cm$^{-1}$.

NMR (DMSO-d$_6$, δ): 1.85 (6H, s), 2.81 and 3.32 (2H, ABq, J=18Hz), 3.87 (3H, s), 5.00 (1H, d, J=5Hz), 5.20 and 5.54 (2H, ABq, J=15Hz), 5.59 (1H, dd, J=5Hz, 8Hz), 6.54 (1H, d, J=3Hz), 7.40 (1H, br s), 7.51 (1H, br s), 7.79 (1H, d, J=1Hz), 8.08 (2H, br s), 8.32 (1H, d, J=3Hz), 9.05 (1H, d, J=1Hz), 9.42 (1H, d, J=8Hz).

(9)

7β-[2-(2-Aminothiazol-4-yl)-2-methoxyiminoacetamido]-3-[1-(1-carbamoyl-1-methylethyl)-5-(1H-imidazo[1,2-b]-pyrazolio)]methyl-3-cephem-4-carboxylate (syn isomer)

IR (Nujol): 1770, 1670, 1610 cm$^{-1}$.

NMR (DMSO-d$_6$, δ): 1.84 (6H, s), 2.80 and 3.37 (2H, ABq, J=18Hz), 3.76 (3H, s), 4.96 (1H, d, J=5Hz), 5.17 and 5.59 (2H, ABq, J=15Hz), 5.53 (1H, dd, J=5Hz, 8Hz), 6.49 (1H, d, J=3Hz), 6.61 (1H, s), 7.08 (2H, br s), 7.37 (1H, br s), 7.45 (1H, br s), 7.73 (1H, br s), 8.27 (1H, d, J=3Hz), 8.97 (1H, br s), 9.40 (1H, d, J=8Hz).

(10)

7β-[2-(5-Amino-1,2,4-thiadiazol-3-yl)-2-methoxyiminoacetamido]-3-[1-(N,N-dimethylcarbamoylmethyl)-1H-imidazo[1,2-b]pyrazolio)]methyl-3-cephem-4-carboxylate (syn isomer)

IR (Nujol): 1770, 1650 1600 cm$^{-1}$.

NMR (DMSO-d$_6$, δ): 2.88 (3H, s), 3.06 (3H, s), 3.43 (2H, br s), 3.87 (3H, s), 5.01 (1H, d, J=5Hz), 5.24 (2H, s), 5.22 and 5.57 (2H, ABq, J=15Hz), 5.60 (1H, dd, J=5Hz, 8Hz), 6.51 (1H, d, J=3Hz), 7.57 (1H, br s), 8.09 (2H, br s), 8.31 (1H, d, J=3Hz), 9.37 (1H, br s), 9.44 (1H, d, J=8Hz).

(11)

7β-[2-(5-Amino-1,2,4-thiadiazol-3-yl)-2-methoxyiminoacetamido]-3-[7-carbamoyl-5-(1H-imidazo-[1,2-b]pyrazolio)]methyl-3-cephem-4-carboxylate (syn isomer)

IR (Nujol): 1780, 1760, 1660, 1610 cm$^{-1}$.

NMR (DMSO-d$_6$, δ): 3.08 and 3.43 (2H, ABq, J=18Hz), 3.89 (3H, ), 5.06 (1H, d, J=5Hz), 5.35 (2H, br s), 5.72 (1H, dd, J=5Hz, 8Hz), 7.43 (2H, br s), 7.50 (1H, br s), 8.07 (2H, br s), 8.25 (1H, br s), 8.50 (1H, s), 9.48 (1H, d, J=8Hz).

(12) 7β-[2-(5-Amino-1,2,4-thiadiazol-3-yl)-2-0 methoxyiminoacetamido]-3-[1-methyl-7-carbamoyl-5-(1H-imidazo[1,2-b]pyrazolio)]methyl-3-cephem-4-carboxylate (syn isomer)

NMR (DMSO-d$_6$, δ): 3.52 (2H, br s), 3.88 (3H, s), 4.10 (3H, s), 5.00 (1H, d, J=5Hz), 5.28 and 5.58 (2H, ABq, J=15Hz), 5.65 (1H, dd, J=5Hz, 8Hz), 7.70 (1H, br s), 8.07 (2H, br s), 8.85 (1H, br s), 9.05 (1H, d, J=1Hz), 9.43 (1H, d, J=8Hz).

(13)

7β-[2-(5-Amino-1,2,4-thiadiazol-3-yl)-2-methoxyiminoacetamido]-3-[1-methyl-7-methoxycarbonyl-5-(1H-imidazo[1,2-b]pyrazolio)]methyl-3-cephem-4-carboxylate (syn isomer)

IR (Nujol): 1770, 1710, 1680, 1610 cm$^{-1}$.

NMR (D$_2$O, δ): 3.17 and 3.50 [2H, ABq, J=18Hz), 3.81 (3H, s), 3.87 (3H, s), 3.93 (3H, s), 5.18 [1H, d, J=5Hz), 5.35 (2H, br s), 5.80 (1H, d, J=5Hz), 7.43 (1H, br s), 8.00 (1H, d, J=2Hz), 8.60 (1H, s)

(14)

7β-[2-(5-Amino-1,2,4-thiadiazol-3-yl)-2-methoxyiminoacetamido]-3-[1-methyl-7-carboxy-5-(1H-imidazo[1,2-b]-pyrazolio)]methyl-3-cephem-4-carboxylate (syn isomer)

IR (Nujol): 1760, 1670, 1600 cm$^{-1}$.

NMR (D$_2$O, δ): 3.16 and 3.45 (2H, ABq, J=18Hz), 4.07 (3H, s), 4.10 (3H, s), 5.20 (1H, d, J=5Hz), 5.31 (2H, br s), 5.83 (1H, d, J=5Hz), 7.37 (1H, br s), 7.91 (1H, d, J=2Hz), 8.26 (1H, s).

(15)

7β-[2-(5-Amino-1,2,4-thiadiazol-3-yl)-2-methoxyiminoacetamido]-3-[7-acetylamino-5-[1H-imidazo[1,2-b]-pyrazolio)]methyl-3-cephem-4-carboxylate (syn isomer)

IR (Nujol): 1770, 1760, 1660, 1600 cm$^{-1}$.

NMR (DMSO-d$_6$, δ): 2.05 (3H, s), 3.01 and 3.33 (2H, ABq, J=18Hz), 3.87 (3H, s), 5.06 (1H, d, J=5Hz), 5.18 and 5.22 (2H, ABq, J=15Hz), 5.71 (1H, dd, J=5Hz, 8Hz), 7.45 (1H, s), 8.13 (2H, br s), 8.23 (1H, s), 8.30 (1H, s), 9.57 (1H, d, J=8Hz), 10.91 (1H, br s)

(16)

7β-[2-(5-Amino-1,2,4-thiadiazol-3-yl)-2-methoxyiminoacetamido]-3-[2-methyl-5-(1H-imidazo[1,2-b]-pyrazolio)]methyl-3-cephem-4-carboxylate (syn isomer)

IR (Nujol): 1760, 1600, 1040 cm$^{-1}$.

NMR (DMSO-d$_6$, δ): 2.32 (3H, s), 2.92 and 3.30 (2H, ABq, J=18Hz), 3.87 (3H, s), 5.02 (1H, d, J=5Hz), 5.26 and 5.45 (2H, ABq, J=15Hz), 5.67 (1H, dd, J=8.5Hz, 5Hz), 6.44 (1H, d, J=3Hz), 8.18 (2H, s), 8.21 (1H, d, J=3Hz), 8.35 (1H, s), 9.54 (1H, d, J=8.5Hz).

(17)
7β-[2-(5-Amino-1,2,4-thiadiazol-3-yl)-2-methoxyiminoacetamido]-3-[1,2-dimethyl-5-(1H-imidazo[1,2-b]pyrazolio)]methyl-3-cephem-4-carboxylate (syn isomer)

IR (Nujol): 1760, 1670, 1600 cm$^{-1}$.

NMR (DMSO-d$_6$, δ): 2.33 (3H, s), 2.83 and 3.30 (2H, ABq, J=18Hz), 3.70 (3H, s), 3.86 (3H, s), 4.96 (1H, d, J=5Hz), 5.20 and 5.50 (2H, ABq, J=15Hz), 5.60 (1H, dd, J=8Hz, 5Hz), 6.57 (1H, d, J=3Hz), 8.10 (2H, s), 6.23 (1H, d, J=3Hz), 8.56 (1H, s), 9.40 (1H, d, J=8Hz)

(18)
7β-[7-methyl-5-(1H-imidazo[1,2-b]pyrazolio)]methyl-3-cephem-4-carboxylate (syn isomer)

IR (Nujol): 1765, 1665, 1605, 1515 cm$^{-1}$.

NMR (D$_2$O, δ): 1.38 (3H, t, J=7Hz), 2.28 (3H, s), 3.17 and 3.42 (2H, ABq, J=18Hz), 4.33 (2H, q, J=7Hz), 5.05-5.40 (2H, m), 5.23 (1H, d, J=5Hz), 5.85 (1H, d, J=5Hz), 6.96 (1H, s), 7.43 (1H, br s), 7.74 (1H, br s), 7.81 (1H, br s)

(19)
7β-[2-55-Amino-1,2,4-thiadiazol-3-yl)-2-ethoxyiminoacetamido]-3-[7-methyl-5-(1H-imidazo[1,2-b]pyrazolio)]methyl-3-cephem-4-carboxylate (syn isomer)

IR (Nujol): 1770, 1670, 1610, 1520 cm$^{-1}$.

NMR (D$_2$O, δ): 1.33 (3H, t, J=7Hz), 2.20 (3H, s), 3.08 and 3.46 (2H, ABq, J=18Hz), 4.32 (2H, q, J=7Hz), 4.98-5.47 (2H, m), 5.20 (1H, d, J=5Hz), 5.80 (1H, d, J=5Hz), 7.35 (1H, br s), 7.63 (1H, br s), 7.70 (1H, d, J=2Hz).

(20)
7β-[2-(5-Amino-1,2,4-thiadiazol-3-yl)-2-allyloxyiminoacetamido]-3-[1,7-dimethyl-5-(1H-imidazo-[1,2-b]pyrazolio)]methyl-3-cephem-4-carboxylate (syn isomer)

IR (Nujol): 1770, 1675, 1605, 1550, 1520 cm$^{-1}$.

NMR (D$_2$O, δ): 2.30 (3H, s), 3.18 and 3.36 (2H, ABq, J=18Hz), 3.88 (3H, s), 5.00-5.25 (2H, m), 5.16 (1H, d, J=5Hz), 5.30-5.60 (2H, m), 5.78 (1H, d, J=5Hz), 5.80-6.20 (1H, m), 7.29 (1H, br s), 7.69 (1H, br s), 7.78 (1H, d, J=3Hz).

(21)
7β-[2-(2-Aminothiazol-4-yl)-2-ethoxyiminoacetamido]-3-[1,7-dimethyl-5-(1H-imidazo[1,2-b]pyrazolio)]methyl-3-cephem-4-carboxylate (syn isomer)

NMR (D$_2$O, δ): 1.30 (3H, t, J=7Hz), 2.31 (3H, s), 3.10 and 3.40 (2H, ABq, J=18Hz), 3.90 (3H, s), 4.25 (2H, q, J=7Hz), 5.03-5.30 (2H, m), 5.18 (1H, d, J=5Hz), 5.76 (1H, d, J=5Hz), 6.88 (1H, s), 7.30 (1H, br s), 7.71 (1H, br s), 7.79 (1H, d, J=3Hz)

(22)
7β-[2-(5-Amino-1,2,4-thiadiazol-3-yl)-2-methoxyiminoacetamido]-3-[1-(N,N-dimethylcarbamoyl)-5-(1H-imidazo[1,2-b]pyrazolio)]methyl-3-cephem-4-carboxylate (syn isomer)

NMR (DMSO-d$_6$, δ): 3.10 (6H, s), 3.28-3.70 (2H, m), 3.87 (3H, s), 5.00 (1H, d, J=5Hz), 5.15-5.68 (2H, m), 5.63 (1H, dd, J=5Hz, 8Hz), 5.67 (1H, d, J=3Hz), 8.01 (1H, d, J=2Hz), 8.10 (2H, br s), 8.53 (1H, d, J=3Hz), 9.16 (1H, d, J=2Hz), 9.45 (1H, d, J=8 Hz).

(23)
7β-[2-(5-Amino-1,2,4-thiadiazol-3-yl)-2-(3-hydroxypropoxyimino)acetamido]-3-[5-(1H-imidazo[1,2-b]pyrazolio)]methyl-3-cephem-4-carboxylate (syn isomer)

IR (Nujol): 1770, 1660, 1595, 1510 cm$^{-1}$.

NMR (DMSO-d$_6$, δ): 1.50-1.88 (2H, m), 2.86 and 3.26 (2H, ABq, J=18Hz), 3.25-3.55 (2H, m), 3.80-4.33 (2H, m), 4.96 (1H, d, J=5Hz), 5.00-5.46 (2H, m), 5.63 (1H, dd, J=5Hz, 8Hz), 6.38 (1H, d, J=3Hz), 7.49 (1H, br s), 8.00 (2H, br s), 8.10 (1H, d, J=3Hz), 8.36 (1H, br s), 9.38 (1H, d, J=8Hz).

(24)
7β-[2-(2-Aminothiazol-4-yl)-2-acetoxyiminoacetamido]-3-[5-(1H-imidazo[1,2-b]pyrazolio)]methyl-3-cephem-4-carboxylate (syn isomer)

NMR (DMSO-d$_6$, δ): 2.10 (3H, s), 3.06-3.38 (2H, m), 4.95-5.28 (2H, m), 5.25 (1H, d, J=5Hz), 5.40-5.60 (1H, m), 6.30-6.45 (1H, m), 6.95 (1H, s), 7.70 (1H, br s), 7.90-8.10 (1H, m), 8.30-8.36 (1H, m)

EXAMPLE 7

To a suspension of 7β-[2-(5-amino-1,2,4-thiadiazol-3-yl)-2-methoxyiminoacetamido]-3-[1-(2-formylaminoethyl)-5-(1H-imidazo[1,2-b]pyrazolio)]methyl-3-carboxylic (syn isomer) (0.74 g) in methanol (4 ml) was added concentrated hydrochloric acid (0.35 ml). The mixture was stirred at room temperature for 20 hours. The reaction mixture was poured into ethyl acetate (100 ml). The resultant precipitate was collected by filtration, washed with isopropyl ether and dried over magnesium sulfate in vacuo to give 7β-[2-(5-amino-1,2,4-thiadiazol-3-yl)-2-methoxyiminoacetamido]-3-[1-(2-aminoethyl)-5-(1H-imidazo[1,2-b]pyrazolio)]methyl-3-cephem-4-carboxylate dihydrochloride (syn isomer) (0.76 g).

IR (Nujol): 1780, 1710, 1670, 1640, 1600 cm$^{-1}$.

NMR (D$_2$O, δ): 3.30 and 3.65 (2H, ABq, J=18Hz), 4.09 (3H, s), 3.47-3.80 (2H m), 4.42-4.70 (2H m), 5.29 (1H, d, J=5Hz), 5.36 and 5.61 (2H, ABq, J=15Hz), 5.89 (1H, d, J=5Hz), 6.62 (1H, d, J=3Hz), 7.57 (1H, br s), 7.97 (1H, d, J=2Hz), 8.12 (1H, d, J=3Hz)

EXAMPLE 8

To a solution of 7β-[2-(2-aminothiazol-4-yl)-2-ethoxyiminoacetamido]-3-[5-(1H-imidazo[1,2-b]pyrazolio)]methyl-3-cephem-4-carboxylate (syn isomer) (13.1 g) in 1M sulfuric acid (30 ml) was added acetone (90 ml) under stirring at 20° C. and the mixture was stirred for 2 hours at the same temperature. The resultant crystals were collected by filtration and dried to give 7β-[2-(2-aminothiazol-4-yl)-2-ethoxyiminoacetamido]-3-[5-(1H-imidazo[1,2-b]pyrazolio)]methyl-3-cephem-4-carboxylate sulfate (syn isomer)(12 g).

IR (Nujol): 3280, 1785, 1680, 1655, 1590, 1520 cm$^{-1}$.

NMR (D$_2$O, δ): 1.20 (3H, t, J=7Hz), 2.93 and 3.35 (2H, ABq, J=18Hz), 4.05 (2H, q, J=7Hz), 5.05 (1H, d, J=5Hz), 5.20-5.50 (2H, m), 5.66 (1H, dd, J=5Hz, 8Hz), 6.45 (1H, d, J=5Hz), 6.68 (1H, s), 7.15 (2H, br s), 7.49-7.62 (1H, m), 8.18 (1H, d, J=5Hz), 8.38-8.55 (1H, m), 9.46 (1H, d, J=8Hz). Example 9

To a solution of 7β-[2-(2-aminothiazol-4-yl)-2-acetoxyiminoacetamido]-3-[5-(1H-imidazo[1,2-b]-pyrazolio)]methyl-3-cephem-4-carboxylate (syn isomer) in a mixture of methanol (20 ml) and water (10 ml). To the solution was added ammonium chloride (622 mg) and the mixture was stirred at 25° C. for 3 hours at pH 8.0.

The reaction mixture was adjusted to pH 3.0 with 1N hydrochloric acid and concentrated to 10 ml under reduced pressure. The concentrate was subjected to column chromatography on Diaion HP-20 using 5% isopropyl alcohol as an eluent and the fraction was lyophilized to give 7β-[2-(2-aminothiazol-4-yl)-2-hydroxyiminoacetamido]-3-[5-(1H-imidazo[1,2-b]pyrazolio)]methyl-3-cephem-4-carboxylate (syn isomer) (2 g).

NMR (DMSO-d$_6$, δ): 2.90 and 3.33 (2H, ABq, J=18 Hz), 5.03 (1H, d, J=5Hz), 5.18-5.60 (2H, m), 5.63 (1H, dd, J=5Hz, 8Hz), 6.45 (1H, d, J=3Hz), 6.60 (1H, s), 7.03 (1H, br s), 7.65 (1H, br s), 8.18 (1H, d, J=3Hz), 8.47 (1H, d, J=2Hz, 9.35 (1H, d, J=8Hz).

EXAMPLE 10

A solution of 7β-[2-(2-aminothiazol-4-yl)-2-ethoxyiminoacetamido]-3-[5-(1H-imidazo[1,2-b]pyrazolio)]-methyl-3-cephem-4-carboxylate sulfate (syn isomer) (1.5 g) in water (80 ml) was adjusted to pH 9.5 with 1N a sodium hydroxide. The solution was subjected to column chromatography on Diaion HP-20 using 20% isopropyl alcohol as an eluent and the object fractions were lyophilized to give sodium 78-[2-(2-aminothiazol-4-yl)-2-ethoxyimino-acetamido]-3-(5H-imidazo[1,2-b]pyrazol-5-yl)methyl-3-cephem-4-carboxylate (syn isomer) (946 mg).

NMR [DMSO-d$_6$, δ): 1.20 (3H, t, J=7Hz), 2.87 and 3.27 (2H, ABq, J=18Hz), 4.05 (2H, q, J=7Hz), 5.05 (1H, d, J=5Hz), 5.05-5.48 (2H m), 5.63 (1H, dd, J=5Hz, 8Hz), 6.24 (1H, d, J=3Hz), 6.65 (1H, s), 7.15 (2H, br s), 7.20-7.35 (1H, m), 7.93 (1H, d, J=3Hz), 8.16-8.33 (1H, m), 9.48 (1H, d, J=8Hz).

EXAMPLE 11

The following compound was obtained by treating 7β-[2-(5-amino-1,2,4-thiadiazol-3-yl)-2-ethoxyiminoacetamido]-3-[5-(1H-imidazo[1,2-b]pyrazolio)]methyl-3-cephem-4-carboxylate (syn isomer) according to a similar manner to that of Example 10.

Sodium 7β-[2-(5-amino-1,2,4-thiadiazol-3-yl)-2-ethoxyiminoacetamido]-3-(5H-imidazo[1,2-b]pyrazol-5-yl)-methyl-3-cephem-4-carboxylate (syn isomer)

NMR (DMSO-d$_6$, δ): 1.20 (3H, d, J=7Hz), 2.85 and 3.18 (2H, ABq, J=18Hz), 4.13 (2H, q, J=7Hz), 5.00 (1H, d, J=5Hz), 5.11-5.25 (2H, m), 5.63 (1H, dd, J=5Hz, 8Hz), 6.21 (1H, d, J=3Hz), 7.23 (1H, d, J=2Hz), 7.91 (1H, d, J=3Hz), 8.16 (2H, br s), 8.25 (1H, d, J=2Hz), 9.54 (1H, d, J=8Hz).

What we claim is:
1. A compound of the formula:

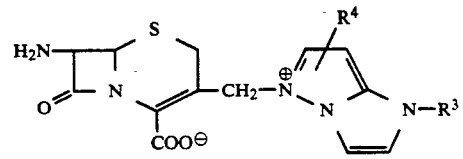

wherein
R$^3$ is hydrogen, lower alkyl, hydroxy(lower)alkyl, protected hydroxy(lower)alkyl, amino(lower)alkyl, protected amino(lower)alkyl, carbamoyl(lower)alkyl, N,N-di(lower)alkylcarbamoyl(lower)alkyl or an imino protective group, and R$^4$ is hydrogen, lower alkyl, carboxy, protected carboxy, amino, protected amino or carbamoyl, or a salt thereof.

* * * * *